United States Patent [19]

Aruga et al.

[11] Patent Number: 5,268,246
[45] Date of Patent: Dec. 7, 1993

[54] ELECTROPHOTOGRAPHIC PHOTOCONDUCTOR WITH PYRENE-RING-CONTAINING OLEFIN COMPOUND FOR USE IN THE SAME

[75] Inventors: Tamotsu Aruga, Mishima; Masaomi Sasaki, Susono; Tomoyuki Shimada; Hiroshi Adachi, both of Numazu, all of Japan

[73] Assignee: Ricoh Company, Ltd., Tokyo, Japan

[21] Appl. No.: 682,324

[22] Filed: Apr. 9, 1991

Related U.S. Application Data

[63] Continuation-in-part of Ser. No. 641,903, Jan. 16, 1991, Pat. No. 5,059,708.

[30] Foreign Application Priority Data

| Apr. 9, 1990 | [JP] | Japan | 2-94812 |
| Apr. 27, 1990 | [JP] | Japan | 2-113510 |
| Jul. 31, 1990 | [JP] | Japan | 2-204599 |
| Jul. 31, 1990 | [JP] | Japan | 2-204600 |

[51] Int. Cl.$^5$ .......................... G03G 5/047
[52] U.S. Cl. ...................... 430/59; 430/58; 430/71; 430/72; 430/73; 430/74; 430/75; 430/76; 430/77; 430/78; 430/79; 430/83
[58] Field of Search ............... 430/58, 59, 71, 72, 430/73, 74, 75, 76, 77, 78, 79, 83

[56] References Cited

U.S. PATENT DOCUMENTS

| 5,034,294 | 7/1991 | Go et al. | 430/59 |
| 5,079,118 | 1/1992 | Kikuchi et al. | 430/59 |

FOREIGN PATENT DOCUMENTS

| 252965 | 10/1989 | Japan | 430/72 |
| 265257 | 10/1989 | Japan | 430/72 |
| 51163 | 2/1990 | Japan | 430/59 |
| 190863 | 7/1990 | Japan | 430/59 |
| 7503583 | 7/1975 | Netherlands | 430/72 |

Primary Examiner—Roland Martin
Attorney, Agent, or Firm—Oblon, Spivak, McClelland, Maier & Neustadt

[57] ABSTRACT

An electrophotographic photoconductor is composed of an electroconductive support and a photoconductive layer formed thereon comprising a novel pyrene-ring-containing olefin compound having formula [I]:

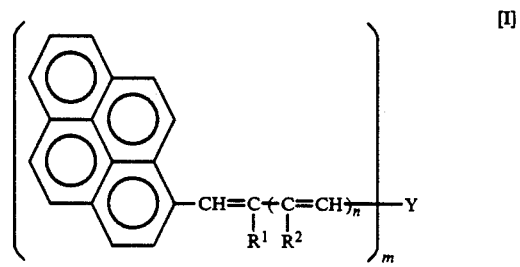

wherein $R^1$ and $R^2$ each represent hydrogen or an alkyl group which may have a substituent; Y is an aliphatic hydrocarbon group which may have a substituent, a cyclic hydrocarbon group which may have a substituent, or an aromatic group which may have a substituent; n is an integer of 0 or 1, and m is an integer of 1 to 3, provided that when n is 0, m is 1, $R^1$ is hydrogen, and Y is an aromatic group with a substituent

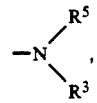

$R^5$ and $R^3$ each represent hydrogen, and Y and $R^1$ may be bonded to form a ring, a method of synthesizing the pyrene-ring-containing olefin compound and an intermediate therefor are disclosed.

22 Claims, 13 Drawing Sheets

ELECTROPHOTOGRAPHIC PHOTOCONDUCTOR WITH PYRENE-RING-CONTAINING OLEFIN COMPOUND FOR USE IN THE SAME

This application is a continuation-in-part of application Ser. No. 07/641,903, filed Jan. 16, 1991, now U.S. Pat. No. 5,059,708.

BACKGROUND OF THE INVENTION

1. Field of the Invention

This invention relates to an electrophotographic photoconductor comprising a pyrene-ring-containing olefin compound in a photoconductive layer thereof, the pyrene-ring-containing olefin compound, an intermediate for synthesizing the olefin compound and a method of synthesizing the olefin compound.

2. Discussion of Background

Conventionally, inorganic materials such as selenium, cadmium sulfide and zinc oxide are used as photoconductive materials of an electrophotographic photoconductor in an electrophotographic process. The electrophotographic process is one of the image forming processes, through which the surface of the photoconductor is charged uniformly in the dark to a predetermined polarity, for instance, by corona charging. The uniformly charged photoconductor is exposed to a light image to selectively dissipate the electric charge of the exposed areas, so that a latent electrostatic image is formed on the photoconductor. The thus formed latent electrostatic image is developed to a visible image by a developer comprising a coloring agent such as a dye and a pigment, and a binder agent such as a polymeric material.

Fundamental characteristics required for the photoconductor in such an electrophotographic process are: (1) chargeability to an appropriate potential in the dark, (2) minimum dissipation of electric charge in the dark, and (3) rapid dissipation of electric charge when exposed to the light.

However, while the above-mentioned inorganic materials have many advantages, they have several shortcomings from the viewpoint of use in practice.

For instance, a selenium photoconductor, which is widely used at present, completely satisfies the above-mentioned requirements (1) to (3), but it has the shortcomings that its manufacturing conditions are difficult to control, and accordingly its production cost is high. In addition, it is difficult to work it into the form of a belt due to its poor flexibility, and it is so vulnerable to heat and mechanical shocks that it must be handled with the utmost care.

A cadmium sulfide photoconductor and a zinc oxide photoconductor can be easily obtained by coating a dispersion of cadmium sulfide particles and zinc oxide particles in a binder resin on a support. However, they are poor in mechanical properties, such as surface smoothness, hardness, tensile strength and wear resistance. Therefore, they cannot be used in the repeated operation, as they are.

To solve the above-mentioned problems of the inorganic materials, various electrophotographic photoconductors employing organic materials are proposed recently and some are put to practical use. For example, there are known a photoconductor comprising poly-N-vinylcarbazole and 2,4,7-trinitrofluorene-9-on, as disclosed in U.S. Pat. No. 3,484,237; a photoconductor prepared by sensitizing poly-N-vinylcarbazole with a pigment of pyrylium salt, as disclosed in Japanese Patent Publication 48-25658; a photoconductor comprising as the main component an organic pigment, as disclosed in Japanese Laid-Open Patent Application 47-37543; a photoconductor comprising as the main component an eutectic crystal complex of a dye and a resin, as disclosed in Japanese Laid-Open Patent Application 7-10735; a photoconductor prepared by sensitizing a triphenylamine compound with a sensitizer pigment, as disclosed in U.S. Pat. No. 3,180,730; a photoconductor comprising an amine derivative as a charge transporting material as disclosed in Japanese Laid-Open Patent Application 57-195254, a photoconductor comprising poly-N-Evinylcarbazole and an amine derivative as a charge transporting material, as disclosed in Japanese Laid-Open Patent Application 58-1155, and photoconductors comprising as a photoconductive material a polyfunctional tertiary amine compound, especially a benzidine compound, as disclosed in U.S. Pat. No. 3,265,496, Japanese Patent Publication 39-11546 and Japanese Laid-Open Patent Application 53-27033.

Although the above photoconductors have excellent characteristics and can be used in practice, they are still unsatisfactory as photoconductors for use in electrophotography.

As the conventional methods for synthesizing olefin compounds, various methods are reported, for instance, in "K. B. Becker; SYNTHESIS 341 (1983)". In particular, as the methods of sysnthesizing pyrene-ring-containing olefin compounds, method (1) utilizing Grignard reaction, method (2) utilizing an Anil synthesis, method (3) utilizing Knoevenage reaction, method (4) utilizing Wittig reaction, and method (5) utilizing Wittig-Horner reaction are described in the above reference.

More specifically, as an example of method (1), styryl pyrene is synthesized by use of benzyl magnesium chloride and formic acid as disclosed in "Rec. trav. chim., 74, 119(1955). As an example of method (2), a method of synthesizing 1-(2-naphthyl)-2-(3-pyrenyl)ethylene is disclosed in "C.A. 71, 71927". As an example of method (3), a method of synthesizing 1-(2,4,6-trinitrostyryl)pyrene from the reaction of pyrene-1-aldehyde and 2,4,6-trinitrotoluene is disclosed in German Laid-Open Patent Application 2,513,190 (1975). These methods (1) to (3), however, have the drawbacks that the reaction conditions are difficult, for instance, the reaction must be carried out in a dehydrating condition at high temperatures, taking a lot of time, and the compounds that can be employed are limited to compounds which are activated by electron attractive substituents.

By sharp contrast to the above methods, method (4) which uses a phosphorous compound is an excellent method for synthesizing olefin compounds under mild conditions. More specifically, this reaction provides olefin compounds by the reaction between phosphonium ylide and carbonyl compounds. For example, Bull. Chem. Soc. Jpn. 44 2231 (1971) and 45 875 (1972) describe a Wittig reaction utilizing as a Witting reagent pyrenyl methyl triphenylphosphonium bromide, which provides olefin compounds which are related to the olefin compound according to the present invention. As mentioned above, this reaction is excellent in the production of the olefin compounds. However, the olefin compound obtained by this reaction is a mixture of cis- and trans-olefin compounds, so that it has the shortcomings that the reactivity of those olefin compounds with certain ketones is low and that it is difficult to eliminate phosphine oxide produced as a side product in an amount equimolar to that of the olefin compound produced.

As an example of method (5), a method of synthesizing a substituted aminostyryl pyrene by the reaction of pyrene aldehyde and diethyl 4-diphenylaminobenzyl-phosphonate is disclosed in Japanese Laid-Open Patent Applications 1-252965 and 1-253753. It is considered that this method is extremely difficult to carry out for use in practice.

SUMMARY OF THE INVENTION

It is therefore a first object of the present invention to provide an electrophotographic photoconductor having good durability, free from the conventional shortcomings, which can completely satisfy all the requirements in the electrophotographic process, and can be easily manufactured at relatively low cost.

A second object of the present invention is to provide novel pyrene-ring-containing olefin compounds which are useful as organic photoconductive materials for use in the above-mentioned electrophotographic photoconductor.

A third object of the present invention is to provide intermediates for synthesizing the above pyrene-ring-containing olefin compounds.

A fourth object of the present invention is to provide a method of synthesizing the pyrene-ring-containing olefin compounds.

The first object of the present invention can be achieved by an electrophotographic photoconductor comprising an electroconductive support and a photoconductive layer formed thereon comprising a pyrene-ring-containing olefin compound having formula [I]:

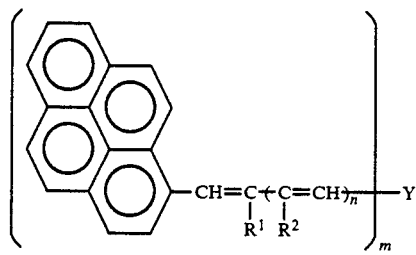

wherein $R^1$ and $R^2$ each represent hydrogen or an alkyl group which may have a substituent; Y is an aliphatic hydrocarbon group which may have a substituent, a cyclic hydrocarbon group which may have a substituent, or an aromatic group which may have a substituent; n is an integer of 0 or 1, and m is an integer of 1 to 3, provided that when n is 0, m is 1, $R^1$ is hydrogen, and Y is an aromatic group with a substituent

$R^5$ and $R^3$ each represent hydrogen, and Y and $R^1$ may be bonded to form a ring.

The second object of the present invention can be achieved by the above-mentioned pyrene-containing olefin compound having formula [I].

The third object of the present invention can be achieved by a phosphonic acid ester of formula [II]:

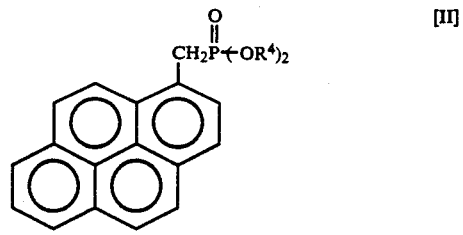

wherein $R^4$ is an alkyl group having 1 to 4 carbon atoms.

The fourth object of the present invention can be achieved by a method of reacting the above phosphonic acid ester of formula [II] with a carbonyl compound of formula III] in the presence of a basic compound in accordance with the following reaction scheme:

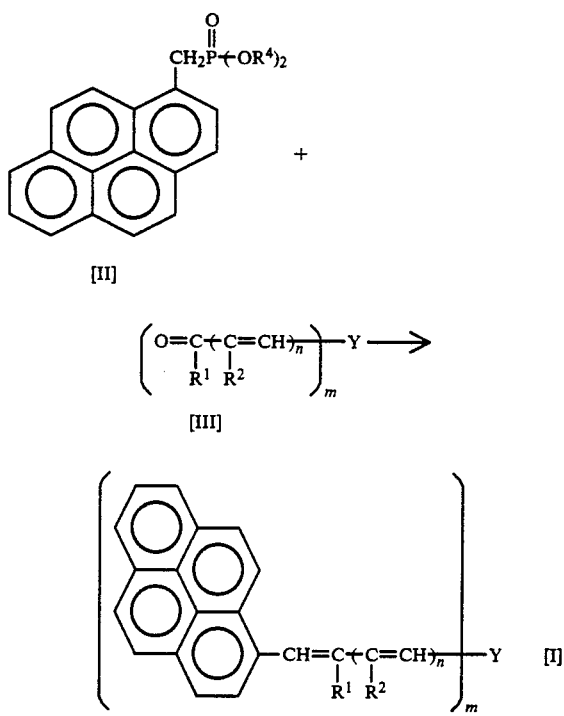

wherein $R^1$, $R^2$, Y, m and n are respectively the same as defined previously, and $R^4$ is an alkyl group having 1 to 4 carbon atoms.

BRIEF DESCRIPTION OF THE DRAWINGS

A more complete appreciation of the invention and many of the attendant advantageous thereof will be readily obtained as the same become better understood by reference to the following detailed description when considered in connection with the accompanying drawings, wherein.

DETAILED DESCRIPTION OF THE PREFERRED EMBODIMENTS

Figure 1:
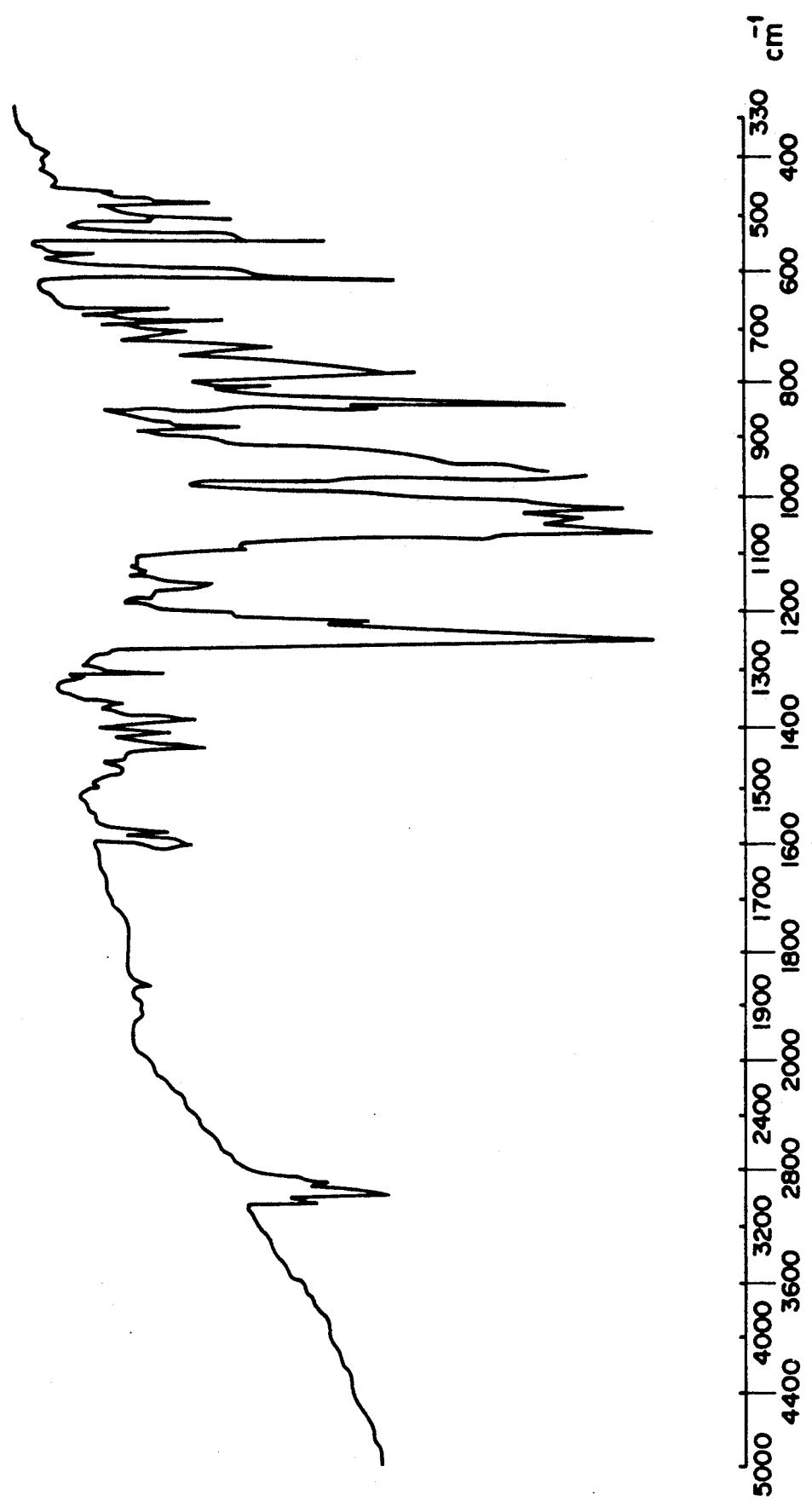
FIG. 1 is an infrared absorption spectrum of diethyl 1-pyrenyl-methyl phosphonate prepared in Example 1.
Figure 2:
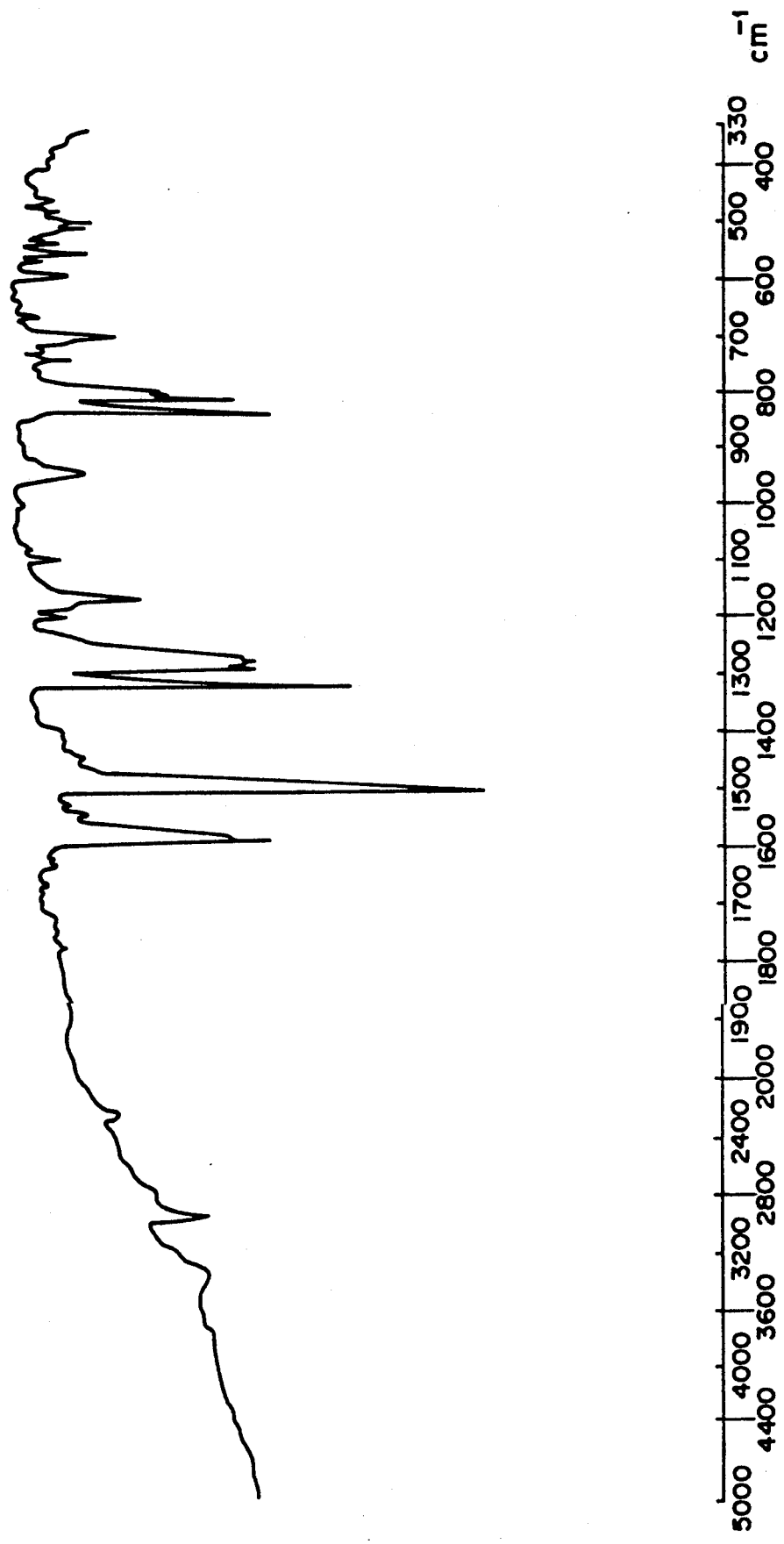
FIG. 2 to FIG. 12 are respectively infrared absorption spectra of pyrene-ring-containing olefin compounds Nos. 2, 3, 6, 7, 10, 16, 17, 18, 19, 21 and 23, taken by the KBr tablet method.
Figure 3:
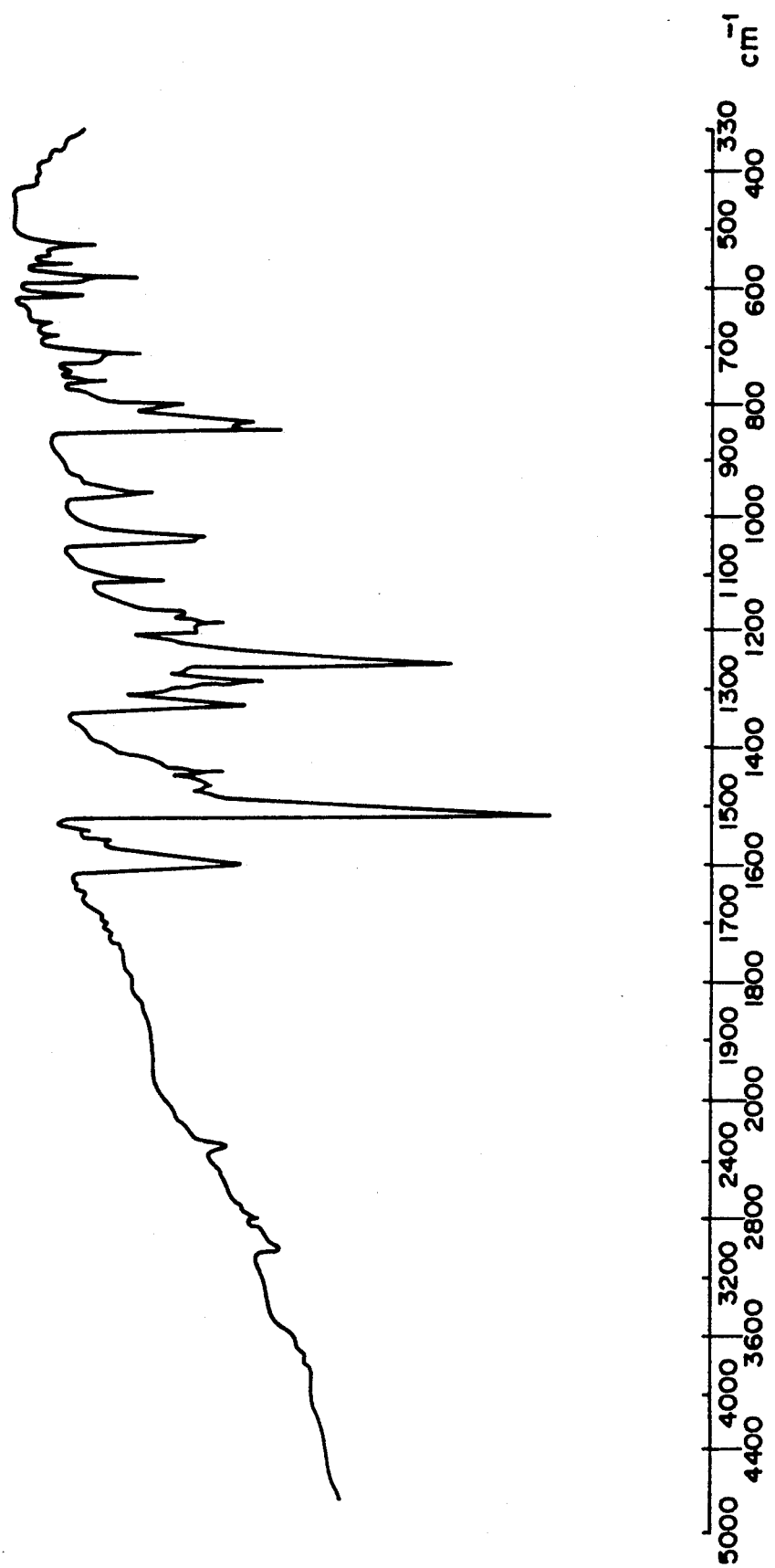
Figure 4:
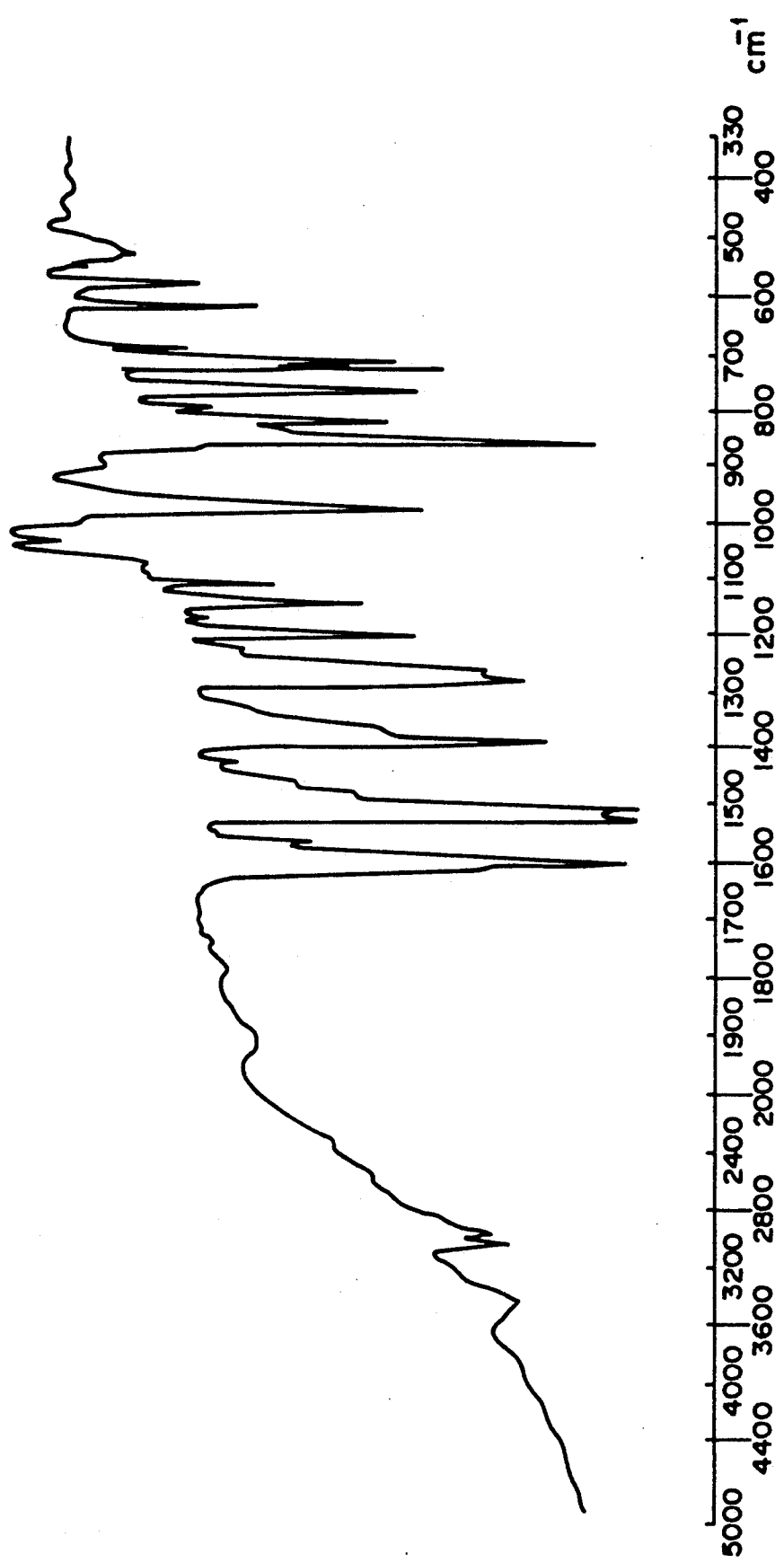
Figure 5:
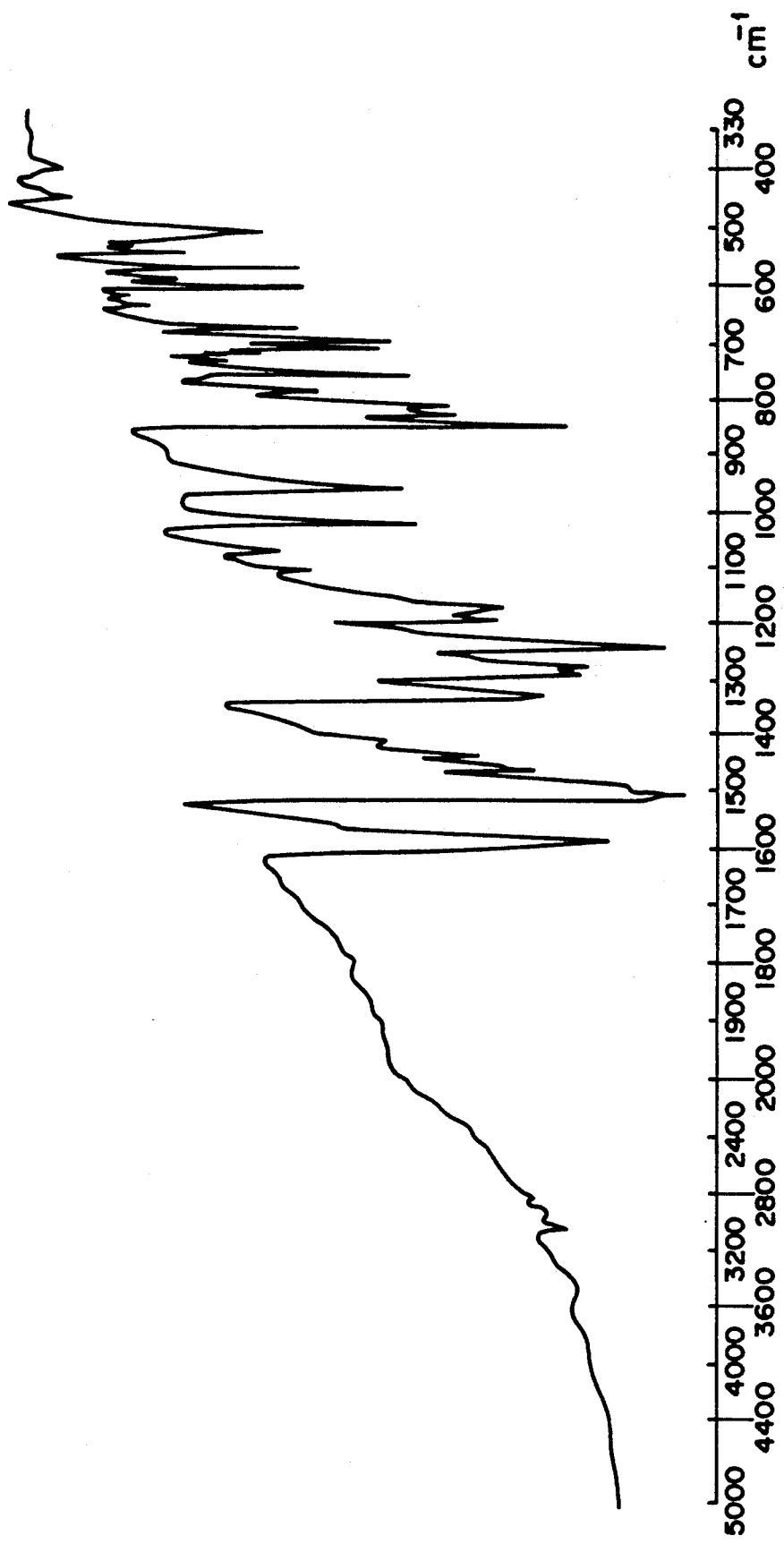
Figure 6:
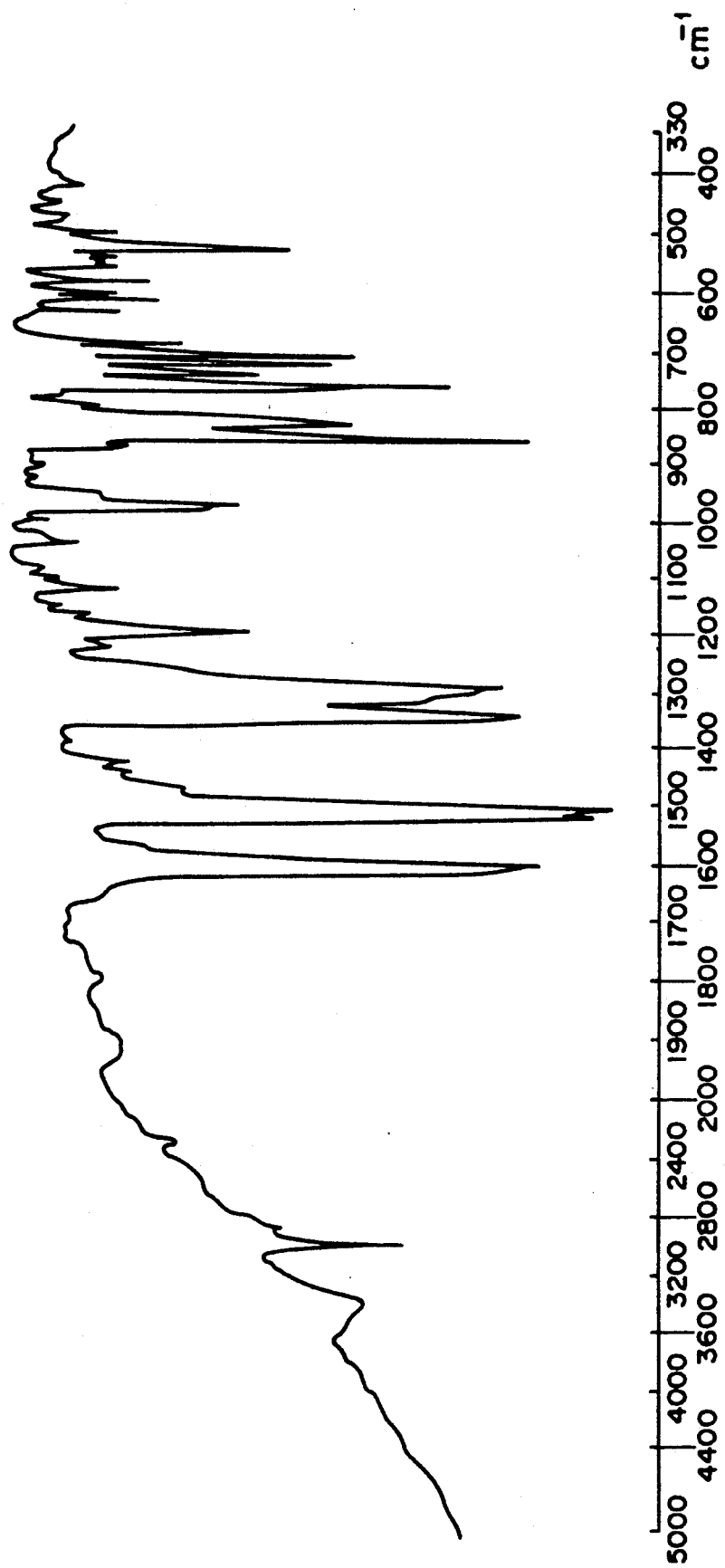

According to the present invention, an electrophotographic photoconductor comprising an electroconductive support and a photoconductive layer formed thereon comprising a pyrene-containing olefin compound having formula [I]:

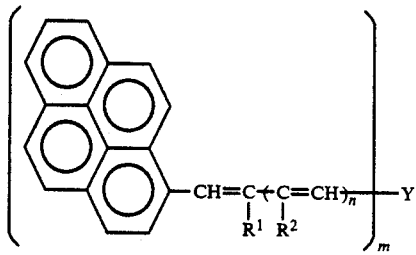

wherein $R^1$ and $R^2$ each represent hydrogen or an alkyl group which may have a substituent; Y is an aliphatic hydrocarbon group which may have a substituent, a cyclic hydrocarbon group which may have a substituent, or an aromatic group which may have a substituent; n is an integer of 0 or 1, and m is an integer of 1 to 3, provided that when n is 0, m is 1, $R^1$ is hydrogen, and Y is an aromatic group with a substituent

$R^5$ and $R^3$ each represent hydrogen, and Y and $R^1$ may be bonded to form a ring.

In the above, the aromatic group represented by Y includes a non-fused carbon cyclic aromatic group such as phenyl group, biphenyl group and terphenyl group; a fused polycyclic hydrocarbon group, and a heterocyclic aromatic group. It is preferable that in the fused polycyclic hydrocarbon group, the number of carbon atoms by which the ring is formed be 18 or less. Specific examples of the fused polycyclic hydrocarbon group include pentalenyl group, indenyl group, naphthyl group, azulenyl group, heptalenyl group, biphenyl group, as-indacenyl group, fluorenyl group, fluorenyl group, s-indacenyl group, acenaphthylenyl group, pleiadenyl group, acenaphthenyl group, phenalenyl group, phenanthrenyl group, anthracenyl group, acephenanthrenyl group, aceanthrylenyl group, triphenylenyl group, pyrenyl group, chrysenyl group, and naphthacenyl group.

Examples of the heterocyclic aromatic group include thienyl group, furyl group, 2-pyridyl group, 4-pyridyl group, 3-indolyl group, 2-thinolynyl group, 3,4-benzpyranyl group, acridinyl group, thiazolyl group, benzthiazolonyl group, 9-methylcarbazolyl group, 9-propylcarbazolyl group, 9-phenylcarbazolyl group, 9-tolylcarbazolyl group.

The above aromatic groups may have a substituent. Examples of the substituent include as follows:

(1) a halogen atom, cyano group, and nitro group; and (2) alkyl group, preferably alkyl group having 1 to 12 carbon atoms, more preferably alkyl group having 1 to 8 carbon atoms, and most preferably alkyl group having 1 to 4 carbon atoms. These alkyl group may further include a fluorine atom, hydroxyl group, cyano group, alkoxyl group having 1 to 4 carbon atoms, phenyl group, or phenyl group which is substituted with a halogen atom, alkyl group having 1 to 4 carbon atoms, or alkoxyl group having 1 to 4 carbon atoms. Specific examples of the alkyl group include methyl group, ethyl group, n-propyl group, i-propyl group, t-butyl group, s-butyl group, n-butyl group, i-butyl group, trifluoromethyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenzyl group and 4-phenylbenzyl group.

(3) alkoxyl group ($-OR^1$), in which $R^1$ is the same alkyl group as that defined in (2) above. Specific examples of the alkoxyl group include methoxy group, ethoxy group, n-propoxy group, i-propoxy group, t-butoxy group, n-butoxy group, s-butoxy group, i-butoxy group, 2-hydroxyethoxy group, 2-cyanoethoxy group, benzyloxy group, 4-methylbenzyloxy group, and trifluoromethoxy group.

(4) aryloxy group. Specific examples of the aryl group in the aryloxy group include phenyl group and naphthyl group. The aryloxy group may have a substituent such as an alkoxy group having 1 to 4 carbon atoms, an alkyl group having 1 to 4 carbon atoms, or a halogen. Specific examples of these aryloxy group include phenoxy group, 1-naphthyloxy group, 2-naphthyloxy group, 4-methylphenoxy group, 4-methoxyphenoxy group, 4-chloro-phenoxy group, and 6-methyl-2-naphthyloxy group.

(5) alkylmercapto group ($-SR^1$), in which $R^1$ is the same alkyl group as that defined in (2) above. Specific examples of the alkylmercapto group include methylthio group, ethylthio group, phenylthio group, and p-methylphenylthio group.

(6)

wherein $R^5$ and $R^3$ each represent hydrogen, the alkyl group defined in (2), or an aryl group, provided that when n is 0, m is 1, and $R^1$ is hydrogen, $R^5$ and $R^3$ each represent hydrogen.

Specific examples of the aryl group include phenyl group and biphenyl group, and naphthyl group. These aryl group may have a substituent such as alkoxyl group having 1 to 4 carbon atoms, alkyl group having 1 to 4 carbon atoms, or a halogen. $R^5$ and $R^3$ may be bonded to each other or to the carbon atoms in the aryl group to form a ring.

Specific examples of the above group include amino group, diethylamino group, diethylamino group, N-methyl-N-phenylamino group, N,N-diphenylamino group, N,N-di(p-tolyl)-amino group, dibenzylamino group, pyperidino group, morpholino group, and juloridyl group.

(7) alkylenedioxy or alkylenedithio group such as methylene dioxy group or methylene dithio group.

The pyrene-ring-containing olefin compounds represented by formula [I] are novel.

Representative examples of the pyrene-ring-containing olefin compound of formula [I] in which $R^2$ is hydrogen that can be used in the present invention are as follows:

TABLE 1

[Pyrene]−CH=C(R¹)−(C(R²)=CH)ₙ−Y]ₘ

| Compound No. | n | m | R¹ | R² | Y |
|---|---|---|---|---|---|
| 1 | 0 | 1 | H | H | −C₆H₄−N(C₆H₅)₂ |
| 2 | 0 | 1 | H | H | −C₆H₄−N(C₆H₄−CH₃)₂ |
| 3 | 0 | 1 | H | H | −C₆H₄−N(C₆H₄−OCH₃)₂ |
| 4 | 0 | 1 | H | H | −C₆H₄−N(C₆H₅)(2,6-dimethylphenyl) |
| 5 | 0 | 1 | H | H | −C₆H₄−N(CH₃)(C₆H₅) |
| 6 | 0 | 1 | H | H | −C₆H₄−N(C₂H₅)(C₆H₅) |
| 7 | 0 | 1 | H | H | −C₆H₄−N(C₆H₅)(C₆H₄−OCH₃) |
| 8 | 0 | 1 | H | H | −C₆H₄−N(CH₂C₆H₅)₂ |
| 9 | 0 | 1 | H | H | −C₆H₄−N(CH₂C₆H₅)(C₆H₅) |
| 10 | 0 | 1 | H | H | −C₆H₄−N(C₆H₅)(C₆H₄−CH₃) |
| 11 | 0 | 1 | H | H | −C₆H₄−N(C₆H₄−CH₃ meta)₂ |
| 12 | 0 | 1 | H | H | −C₆H₄−N(Et)(Et) |
| 13 | 0 | 1 | H | H | −C₆H₅ |
| 14 | 0 | 1 | H | H | −C₆H₄−CH₃ |
| 15 | 0 | 1 | H | H | −C₆H₄−OCH₃ |
| 16 | 0 | 1 | H | H | −C₆H₄−Cl |
| 17 | 1 | 1 | H | H | −C₆H₄−N(CH₃)₂ |
| 18 | 1 | 1 | H | H | −C₆H₄−N(C₆H₅)₂ |
| 19 | 0 | 1 | CH₃ | H | −C₆H₄−Cl |
| 20 | 0 | 1 | CH₃ | H | −C₆H₄−N(C₆H₅)₂ |
| 21 | 0 | 1 | H | H | −pyrenyl |
| 22 | 0 | 1 | H | H | −C₆H₄−CH=CH−pyrenyl |
| 23 | 0 | 2 | H | H | −C₆H₄− |

TABLE 1-continued $$\left[ \underset{\text{pyrene}}{\text{Py}} - CH = C \underset{R^1}{\overset{}{-}} (C = CH)_n \right]_m Y$$

| Compound No. | n | m | $R^1$ | $R^2$ | Y |
|---|---|---|---|---|---|
| 24 | 0 | 2 | H | H | 2,4-dimethylphenyl |
| 25 | 0 | 2 | H | H | o-tolyl (methylphenyl) |
| 26 | 0 | 2 | H | H | 2,5-dimethoxyphenyl (OCH$_3$, OCH$_3$) |
| 27 | 0 | 2 | H | H | 4,4'-N,N-di(p-tolyl)-N-phenylamino |
| 28 | 0 | 1 | CH$_3$ | H | 4-cyanophenyl |
| 29 | 0 | 1 | H | H | 4-(N,N-diphenylamino)naphthyl |
| 30 | 0 | 1 | H | H | 4-[N,N-di(p-tolyl)amino]naphthyl |
| 31 | 0 | 1 | H | H | 4-(N,N-diphenylamino)-1-methylnaphthyl |
| 32 | 0 | 1 | H | H | 4-methoxy-1-methylnaphthyl |
| 33 | 0 | 1 | H | H | 1-methylanthryl |
| 34 | 0 | 1 | H | H | N-(p-chlorophenyl)-N-phenylaminophenyl |
| 35 | 0 | 1 | H | H | 3-methyl-4-(N,N-diphenylamino)phenyl |
| 36 | 0 | 1 | H | H | 4-cyanophenyl (CN) |
| 37 | 0 | 1 | H | H | 2-cyanophenyl (CN) |
| 38 | 0 | 1 | H | H | 4-(methylthio)phenyl (SCH$_3$) |
| 39 | 0 | 1 | H | H | anthryl |
| 40 | 0 | 1 | H | H | 4-(methoxycarbonyl)phenyl (COOCH$_3$) |
| 41 | 0 | 1 | H | H | N-ethylcarbazolyl (C$_2$H$_5$) |
| 42 | 1 | 1 | H | H | 4-(N,N-dimethylamino)phenyl (N(CH$_3$)$_2$) |
| 43 | 0 | 1 | H | H | 2-methoxy-1-methylnaphthyl (OCH$_3$) |
| 44 | 0 | 1 | H | H | 3-chloro-4-(N,N-dimethylamino)phenyl (N(CH$_3$)$_2$, Cl) |
| 45 | 1 | 1 | H | H | 2-methoxyphenyl (OCH$_3$) |
| 46 | 1 | 1 | H | CH$_3$ | phenyl |

In the phosphonic acid ester of formula [II] which serves as an intermediate for synthesizing the pyrene-ring-containing olefin compound of formula [I], $R^1$ is an alkyl group having 1 to 4 carbon atoms. Specific examples of the alkyl group are methyl group, ethyl group, propyl group, isopropyl group, n-butyl group, iso-butyl group, sec-butyl group, and tert-butyl group.

The phosphonic acid ester of formula [II] can be prepared in accordance with the following reaction scheme:

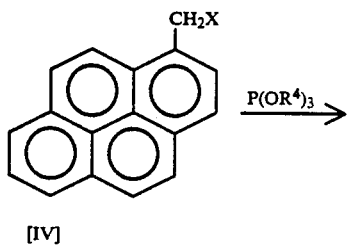

[IV]

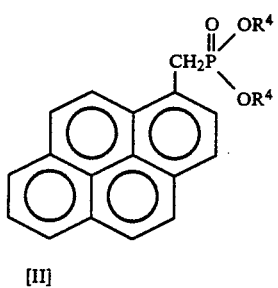

[II]

wherein R⁴ is the same as that defined in formula [II].

In the above reaction, a halomethyl compound of formula [IV], which is a starting material for synthesizing the phosphonic acid ester of formula [II], can be prepared by a conventional method. Further, in this reaction, the reaction between the halomethyl compound of formula [IV] and the trialkyl phosphite of P(OR¹)₃ is carried out without solvent, generally at 80° C. to 160° C., preferably at 100° C. to 140° C., with the molar ratio of the trialkyl phosphite to the halomethyl compound [IV] generally being 1 to 100 : 1, preferably 2 to 4 : 1.

The pyrene-ring-containing olefin compound of formula [I] can be synthesized by allowing the above phosphonic acid ester of formula [II] with a carbonyl compound of formula [III] in the presence of a basic compound in accordance with the following reaction scheme:

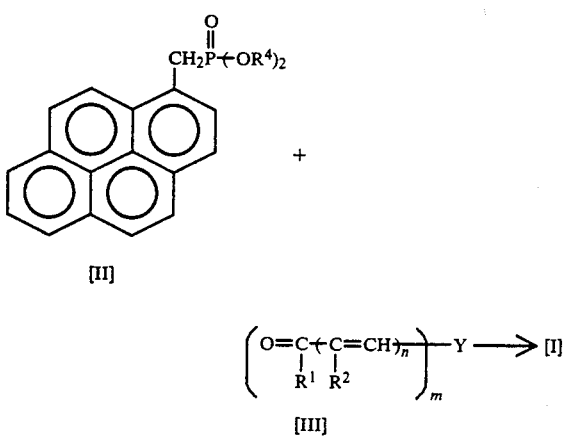

wherein R¹, R², Y, m and n are respectively the same as defined previously, and R⁴ is an alkyl group having 1 to 4 carbon atoms.

In the above reaction, since the phosphonic acid ester of formula [II] has strong neucleophic properties, it can react with varieties of aldehyde and ketones under mild conditions to produce the olefin compounds of the formula [I] selectively in a trans form with high purity and high yield. Furthermore, a phosphine compound produced as a side product in the above reaction is water-soluble, so that the elimination of the side product is easy.

As the basic compound for use in the above reaction, alkoxides of an alkali metal such as lithium and sodium, alkyl alkali metals, and alkali metal hydrides can be employed. As the solvent for use in the above reaction, polar solvents such as N,N-dimethylformamide and dimethyl-sulfoxide, and non-polar solvents such as ethanol, benzene, and tetrahydrofuran can be employed.

When preparing the olefin compound of formula [I] in practice, the phosphonic acid ester of formula [II] and the carbonyl compound of formula [III] are dissolved in any of the above solvents. To this mixture, any of the above basic compounds is gradually added with stirring. The reaction easily proceeds at room temperature.

Examples of the carbonyl compound of formula [III], in which Y is an aliphatic hydrocarbon, include saturated aldehydes such as acetaldehyde, propyonaldehyde, butanal, 2-methylpropanal, pentanal, hexanal, heptanal, octanal, nonanal, and decanal; unsaturated aldehydes such as acrylaldehyde, crotonaldehyde, methacrylaldehyde, 2-methyl-2-butenal, propynal, and 2-butynal; and unsaturated ketones such as ethylidene acetone. These compounds may have the same substituents as set forth in the case of the aromatic groups represented by Y in formula [I]. Examples of such compounds are phenyl acetaldehyde and cinnamaldehyde.

Further examples of the carbonyl compound of formula [III], in which Y is an aliphatic hydrocarbon, include cyclohexane carbaldehyde, safranal, α-ionone, cyclohexanone, 2-cyclohexene-1-on.

The alkyl group represented by R¹ or R² in formula [III] is the same as defined in formula [I].

Examples of the aryl group represented by R¹ or R² in formula [III] are phenyl group, biphenyl group and naphthyl group.

Representative examples of the carbonyl compound of formula [III] when m is 2 are phthalaldehyde, isophthalaldehyde, terephthalaldehyde, naphthalenedicarbaldehyde, 2,4-hexadiene-1,6-dial.

Representative examples of the carbonyl compound of formula [III] when m is 3 are 1,3,5-triacetylbenzene and 4,4',4''-triacetyltriphenylamine.

The above-mentioned olefin compounds for use in the present invention are remarkably effective as photoconductive materials in the electrophotographic photoconductor and can be optically or chemically sensitized with a sensitizer such as a dye or Lewis acid. In addition, the olefin compounds effectively function as charge transporting materials in a function-separating type electrophotographic photoconductor where an organic or inorganic pigment serves as a charge generating material.

In the photoconductors according to the present invention, at least one olefin compound of formula [I] is contained in the photoconductive layers 2, 2a, 2b, 2c, 2d and 2e. The olefin compounds can be employed in different ways, for example, as shown in FIG. 13 through FIG. 18.

Figure 13:
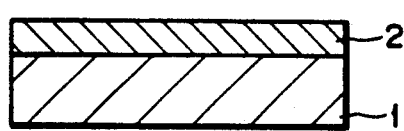
FIG. 13 is a schematic cross-sectional view of an electrophotographic photoconductor according to the present invention.

In the photoconductor as shown in FIG. 13, a photoconductive layer 2 is formed on an electroconductive support 1, which photoconductive layer 2 comprises a pyrene-ring-containing olefin compound, a sensitizing dye and a binder agent or binder resin. In this photoconductor, the pyrene-ring-containing olefin compound works as a photoconductive material, through which charge carriers necessary for the light decay of the photoconductor are generated and transported. However, the pyrene-ring-containing olefin compound itself scarcely absorbs light in the visible light range and, therefore, it is necessary to add a sensitizing dye which absorbs light in the visible light range in order to form latent electrostatic images by use of visible light.

Figure 14:
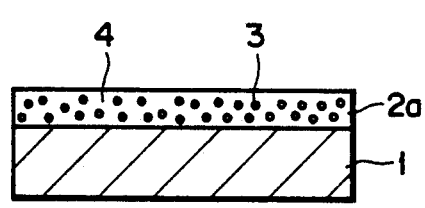

Referring to FIG. 14, there is shown an enlarged cross-sectional view of another embodiment of an electrophotographic photoconductor according to the present invention. In the figure, reference numeral 1 indicates an electroconductive support. On the electroconductive support 1, there is forced a photoconductive layer 2a comprising a charge generating material 3 dispersed in a charge transporting medium 4 comprising a pyrene-ring-containing olefin compound and a binder agent. In this embodiment, the pyrene-ring-containing olefin compound and the binder agent (or a mixture of the binder agent and a plasticizer) constitute the charge transporting medium 4 in combination. The charge generating material 3, which is, for example, an inorganic or organic pigment, generates charge carriers The charge transporting medium 4 accepts the charge carriers generated by the charge generating material 3 and transports those charge carriers.

In this electrophotographic photoconductor, it is basically required that the light-absorption wavelength regions of the charge generating material 3 and the pyrene-ring-containing olefin compound do not overlap in the visible light range. This is because, in order that the charge generating material 3 produce charge carriers efficiently, it is necessary that light pass through the charge transporting medium 4 and reach the surface of the charge generating material 3. Since the olefin compounds of the previously described formula [I] do not substantially absorb light in the visible range, they can work effectively as charge transporting materials in combination with the charge generating material 3 which absorbs the light in the visible region and generates charge carriers.

Figure 15:
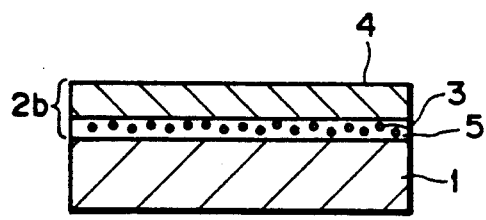

Referring to FIG. 15, there is shown an enlarged cross-sectional view of a further embodiment of an electrophotographic photoconductor according to the present invention. In the figure, there is formed on an electroconductive support 1 a two-layered photoconductive layer 2b comprising a charge generation layer 5 containing a charge generating material 3, and a charge transport layer 4 containing a pyrene-ring-containing olefin compound of the previously described formula [I].

In this photoconductor, light which has passed through the charge transport layer 4 reaches the charge generation layer 5, and charge carriers are generated within the charge generation layer 5. The charge carriers which are necessary for the light decay for latent electrostatic image formation are generated by the charge generating material 3, accepted and transported by the charge transport layer 4. In the charge transport layer 4, the pyrene-ring-containing olefin compound mainly works for transporting charge carriers. The generation and transportation of the charge carriers are performed by the same mechanism as that in the photoconductor shown in FIG. 14.

Figure 16:
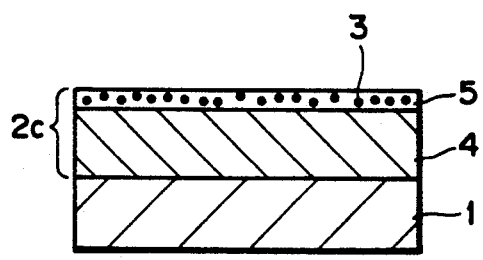
FIG. 14 through 17 are schematic cross-sectional views of other preferred electrophotographic photoconductors according to the present invention.

In an electrophotographic photoconductor shown in FIG. 16, a charge generation layer 5 is formed on a charge transport layer 4 containing a pyrene-ring-containing olefin compound in a photoconductive layer 2c, thus the overlaying order of the charge generation layer 5 and the charge transport layer 4 is reversed as compared with the electrophotographic photoconductor as shown in FIG. 15. The mechanism of the generation and transportation of charge carriers is substantially the same as that of the photoconductor shown in FIG. 15.

Figure 17:
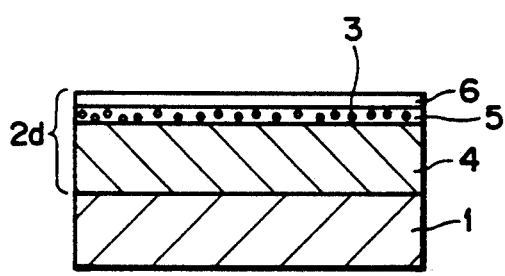

In the above photoconductor, a protective layer 6 may be formed on the charge generation layer 5 as shown in FIG. 17 for protecting the charge generation layer 5.

When the electrophotographic photoconductor according to the present invention as shown in FIG. 13 is prepared, at least one pyrene-ring-containing olefin compound of the previously described formula [I] is dispersed in a binder resin solution, and a sensitizing dye is then added to the mixture, so that a photoconductive layer coating liquid is prepared. The thus prepared photoconductive layer coating liquid is coated on an electroconductive support 1 and dried, so that a photoconductive layer 2 is formed on the electroconductive support 1.

It is preferable that the thickness of the photoconductive layer 2 be in the range of 3 to 50 μm, more preferably in the range of 5 to 20 μm. It is preferable that the amount of the pyrene-ring-containing olefin compound contained in the photoconductive layer 2 be in the range or 30 to 70 wt.%, more preferably about 50 wt.%.

It is preferable that the amount of the sensitizing dye contained in the photoconductive layer 2 be in the range of 0.1 to 5 wt.%, more preferably in the range of 0.5 to 3 wt.%.

Specific examples of the sensitizing dye for use in the present invention include triarylmethane dyes such as Brilliant Green, Victoria Blue B, Methyl Violet, Crystal Violet and Acid Violet 6B; xanthene dyes such as Rhodamine B, Rhodamine 6G, Rhodamine G Extra, Eosin S, Erythrosin, Rose Bengale and Fluoresceine; thiazine dyes such as Methylene Blue; cyanine dyes such as cyanin; and pyrylium dyes such as 2,6-diphenyl-4-(N,N-dimethylaminophenyl)-thiapyrylium perchlorate and benzopyrylium salts disclosed in Japanese Patent Publication 48-25658.

These sensitizing dyes may be used either alone or in combination.

The electrophotographic photoconductor shown in FIG. 14 can be obtained by dispersing finely-divided particles of the charge generating material 3 in a solution in which at least one pyrene-ring-containing olefin compound for use in the present invention and the binder agent are dissolved, coating the above-prepared dispersion on the electroconductive support 1 and then drying the same to form the photoconductive layer 2a.

It is preferable that the thickness of the photoconductive layer 2a be in the range of 3 to 50 μm, more preferably in the range of 5 to 20 μm. It is preferable that the amount of the pyrene-ring-containing olefin compound contained in the photoconductive layer 2a be in the range of 10 to 95 wt.%, more preferably in the range of 30 to 90 wt.%.

It is preferable that the amount of the charge generating material 3 contained in the photoconductive layer 2a be in the range of 0.1 to 50 wt.%, more preferably in the range of 1 to 20 wt.%.

Specific examples of the charge generating material 3 for use in the present invention include inorganic pigments such as selenium, selenium—tellurium, cadmium sulfide, cadmium sulfide—selenium and α-silicon; and organic pigments, such as C.I. Pigment Blue 25 (C.I. 21180), C.I. Pigment Red 41 (C.I. 21200), C.I. Acid Red 52 (C.I. 45100), and C.I. Basic Red 3 (C.I. 45210); an azo pigment having a carbazole skeleton (Japanese Laid-Open Patent Application 53-95033), an azo pigment having a distyryl benzene skeleton [Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); a phthalocyanine pigment such as C.I. Pigment Blue 16 (C.I. 74100); indigo pigments such as C.I. Vat Brown 5 (C.I. 73410) and C.I. Vat Dye (C.I. 73030); and perylene pigments such as Algol Scarlet B and Indanthrene Scarlet R (both made by Bayer Co., Ltd.). These charge generating materials may be used either alone or in combination.

The electrophotographic photoconductor shown in FIG. 15 can be obtained as follows:

The charge generating material is vacuum-deposited on the electroconductive support 1, or the dispersion in which finely-divided particles of the charge generating material 3 are dispersed in an appropriate solvent, if necessary, together with the binder agent is coated on the electroconductive support 1 and dried, so that the charge generation layer 5 is formed. When necessary, the charge generation layer 5 is subjected to buffing to adjust the thickness thereof. On the thus formed charge generation layer 5, the coating solution in which at least one pyrene-ring-containing olefin compound and the binder agent are dissolved is coated and dried, so that the charge transport layer 4 is formed. In the charge generation layer 5, the same charge generating material as employed in the above-mentioned photoconductive layer 2a can be used.

The thickness of the charge generation layer 5 is 5 μm or less, more preferably 2 μm or less. It is preferable that the thickness of the charge transport layer 4 be in the range of 3 to 50 μm, more preferably in the range of 5 to 20 μm. When the charge generation layer 5 is obtained by coating the dispersion in which finely-divided particles of the charge generating material 3 are dispersed in an appropriate solvent together with the binder agent, it is preferable that the amount of finely-divided particles of the charge generating material 3 contained in the charge generation layer 5 be in the range of 10 to 95 wt.%, more preferably in the range of about 50 to 90 wt.%. It is preferable that the amount of the pyrene-ring-containing olefin compound contained in the charge transport layer 4 be in the range of 10 to 95 wt.%, more preferably in the range of 30 to 90 wt.%.

The electrophotographic photoconductor shown in FIG. 16 can be obtained as follows:

The coating solution in which the pyrene-ring-containing olefin compound and the binder agent are dissolved is coated on the electroconductive support 1 and dried to form the charge transport layer 4. On the thus formed charge transport layer 4, the dispersion prepared by dispersing finely-divided particles of the charge generating material 3 in the solvent, in which the binder agent is dissolved when necessary, is coated by spray coating and dried to form the charge generation layer 5 on the charge transport layer 4. The amount ratio of the components contained in the charge generation layer and charge transport layer is the same as previously described in FIG. 15.

The electrophotographic photoconductor shown in FIG. 17 can be obtained by forming a protective layer 6 on the charge generation layer 5 as obtained in FIG. 16 by spraycoating of an appropriate resin solution. As the resins employed in the protective layer 6, the binder agents which will be described later can be used.

Specific examples of the electroconductive support for the electrophotographic photoconductor according to the present invention include a metallic plate or foil made of aluminum, a plastic film on which a metal such as aluminum is deposited, and a sheet of paper which has been treated so as to be electroconductive.

Specific examples of the binder agent for use in the present invention are condensation resins such as polyamide, polyurethane, polyester, epoxy resin, polyketone and polycarbonate; and vinyl copolymers such as polyvinylketone, polystyrene, poly-N-vinylcarbazole and polyacrylamide. All the resins having insulating properties and adhesive force can be employed. Some plasticizers may be added to the above-mentioned binder agent, when necessary. Examples of the plasticizer for use in the present invention are halogenated paraffin, polybiphenyl chloride, dimethylnaphthalene and dibutyl phthalate.

Furthermore, in the electrophotographic photoconductors according to the present invention, an adhesive layer or barrier layer may be interposed between the electroconductive support and the photoconductive layer when necessary. Examples of the material for use in the adhesive layer or barrier layer are polyamide, nitrocellulose and aluminum oxide. It is preferable that the thickness of the adhesive layer or barrier layer be 1 μm or less.

When copying is performed by use of the photoconductors according to the present invention, the surface of the photoconductor is charged uniformly in the dark to a predetermined polarity. The uniformly charged photoconductor is exposed to a light image so that a latent electrostatic image is formed on the photoconductor. The thus formed latent electrostatic image is developed by a developer to a visible image, and when necessary, the developed image can be transferred to a sheet of paper. The electrophotographic photoconductors according to the present invention have high photosensitivity and improved flexibility.

Other features of this invention will become apparent in the course of the following description of exemplary embodiments, which are given for illustration of the invention and are not intended to be limiting thereof.

EXAMPLE 1

Preparation of Diethyl 1-pyrenylmethyl phosphonate 120 g (0.48 moles) of 1-chloromethylprene was dissolved in 500 ml of triethyl phosphite. This reaction mixture was then heated with stirring at 125° C. to 140° C. for 5 hours. In the course of this reaction, ethylene chloride generated was removed from the reaction mixture. The reaction mixture was then cooled. 370 ml of n-hexane was then added to the reaction mixture, so that crystals were caused to separate out. The crystalline product was separated from the reaction mixture by filtration, washed with 300 ml of n-hexane two time, and dried with application of heat under reduced pressure, whereby 151.4 g (89.7%) of a crude product of diethyl 1-pyrenylmethyl phosphonate was obtained. The thus obtained crude product of diethyl 1-pyrenylmethyl phosphonate was recrystallized from a mixed solvent of n-hexane and ethyl acetate, whereby pure diethyl 1-pyrenyl phosphonate was obtained in the form of white needles with a melting point of 115.0° C. to 116.0° C.

The results of elemental analysis of the diethyl 1-pyrenyl phosphonate were as follows:

|      | Found | Calculated |
| ---- | ----- | ---------- |
| % C  | 71.66 | 71.58      |
| % H  | 5.95  | 6.01       |

The infrared spectrum thereof, which is shown in FIG. 1, was measured by use of a KBr tablet. The characteristic absorptions were found at 1245 cm$^{-1}$ ($\gamma_{p=o}$), 1150 cm$^{-1}$ ($\gamma_{c\text{-}o\text{-}(p)}$), and 1025 cm$^{-1}$ ($\gamma_{p\text{-}o\text{-}(c)}$).

EXAMPLE 2

Preparation of N,N-bis(4-methoxyphenyl)-1-(4-aminostyryl)-pyrene (Olefin Compound No. 3)

3.17 g (9 mmol) of diethyl 1-pyrenylmethylphosphonate and 3.0 g (0 mmol) of 4,4'-dimethoxy-4''-formyltriphenylamine were dissolved in 20 ml of N,N-dimethylformamide. To this reaction mixture, 2.08 g (9×1.2 mmol) of sodium methylate (28 wt.% methanol solution of sodium methylate) was gradually added in such a manner that the temperature of the reaction mixture did not exceed 30° C. The reaction mixture was then stirred at room temperature for 2 hours, neutralized with acetic acid, and diluted with about 300 ml of water. The reaction mixture was extracted with toluene. The extract toluene layer was washed with water and dried. The solvent of the reaction mixture was distilled away under reduced pressure, whereby a yellow power was obtained. The thus obtained yellow powder was purified by column chromatography on a column of silica gel, using toluene as the eluent, whereby a yellow powder was obtained with a yield of 4.34 g (90.8%).

The thus obtained yellow powder was recrystallized from a mixed solvent of toluene and n-hexane, whereby N,N-bis(4-methoxyphenyl)-1-(4-aminostyryl)pyrene was obtained in the form of yellow needles. The melting point was 159.7°–160.5° C.

The results of elemental analysis of the N,Nbis-(4-methoxyphenyl)-1-(4-aminostyryl)pyrene were as follows:

|      | Found | Calculated |
| ---- | ----- | ---------- |
| % C  | 85.88 | 85.85      |
| % H  | 5.26  | 5.50       |

The infrared spectrum thereof was measured by use of a KBr tablet. A characteristic absorption was at 960 cm$^{-1}$ ($\delta_{CH,\ trans\text{-}olefin}$).

EXAMPLE 3

Preparation of 1-(4-chlorostyryl)pyrene (Olefin Compound No. 16)

2.47 g (7 mmol) of diethyl 1-pyrenylmethylphosphonate and 0.99 g (7 mmol) of 4-chlorobenzaldehyde were dissolved with stirring in 25 ml of N,N-dimethylformamide. To this reaction mixture, 1.62 g (7×1.2 mmol) of sodium methylate (28 wt.% methanol solution of sodium methylate) was gradually added in such a manner that the temperature of the reaction mixture did not exceed 30° C. The reaction mixture was then stirred at room temperature for 1 hour, neutralized with acetic acid, and diluted with about 300 ml of water. Crystals separated out. The crystals were separated by filtration, washed with water, dried and then purified by column chromatography two times. In the first time, the purification was carried out on a column of silica gel, using a mixed solvent of toluene/n-hexane (1/1) as the developing solvent, and in the second time, the purification was carried out on a column of silica gel, using a mixed solvent of toluene/n-hexane (1/2) as the developing solvent, whereby yellow 1-(4-chlorostyryl)pyrene was obtained with a yield of 2.21 g (93.5%).

The thus obtained 1-(4-chlorostyryl)pyrene was recrystallized from a mixed solvent of toluene and n-hexane, so that pyrene-ring containing olefin compound No. 16 according to the present invention, 1-(4-chlorostyryl)pyrene with a melting point of 157.5° C. to 158.5° C., was obtained in the form of yellow cotton-thread-like needles.

The results of elemental analysis of the 1-(4-chlorostyryl)pyrene were as follows:

|      | Found | Calculated |
| ---- | ----- | ---------- |
| % C  | 85.25 | 85.06      |
| % H  | 4.17  | 4.46       |

Figure 7:
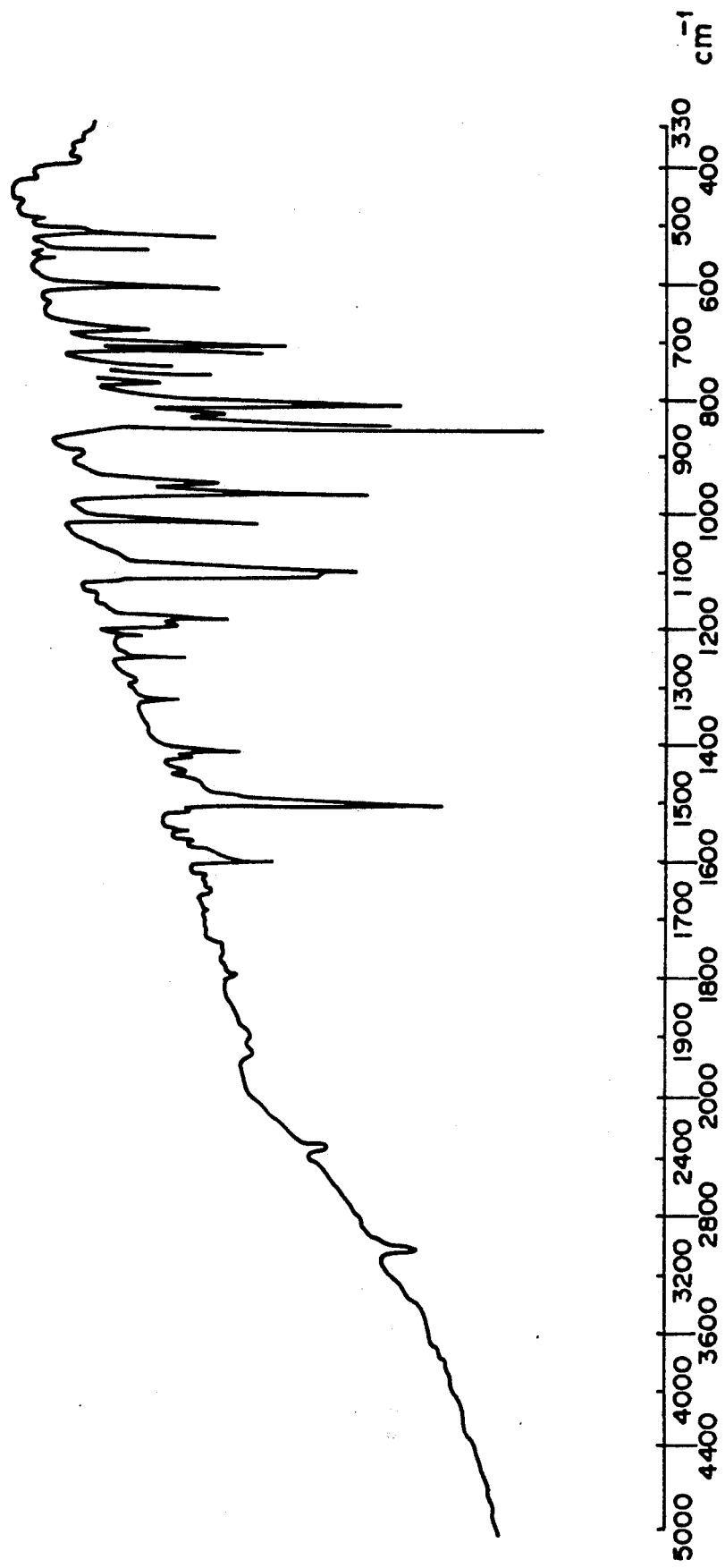
Figure 8:
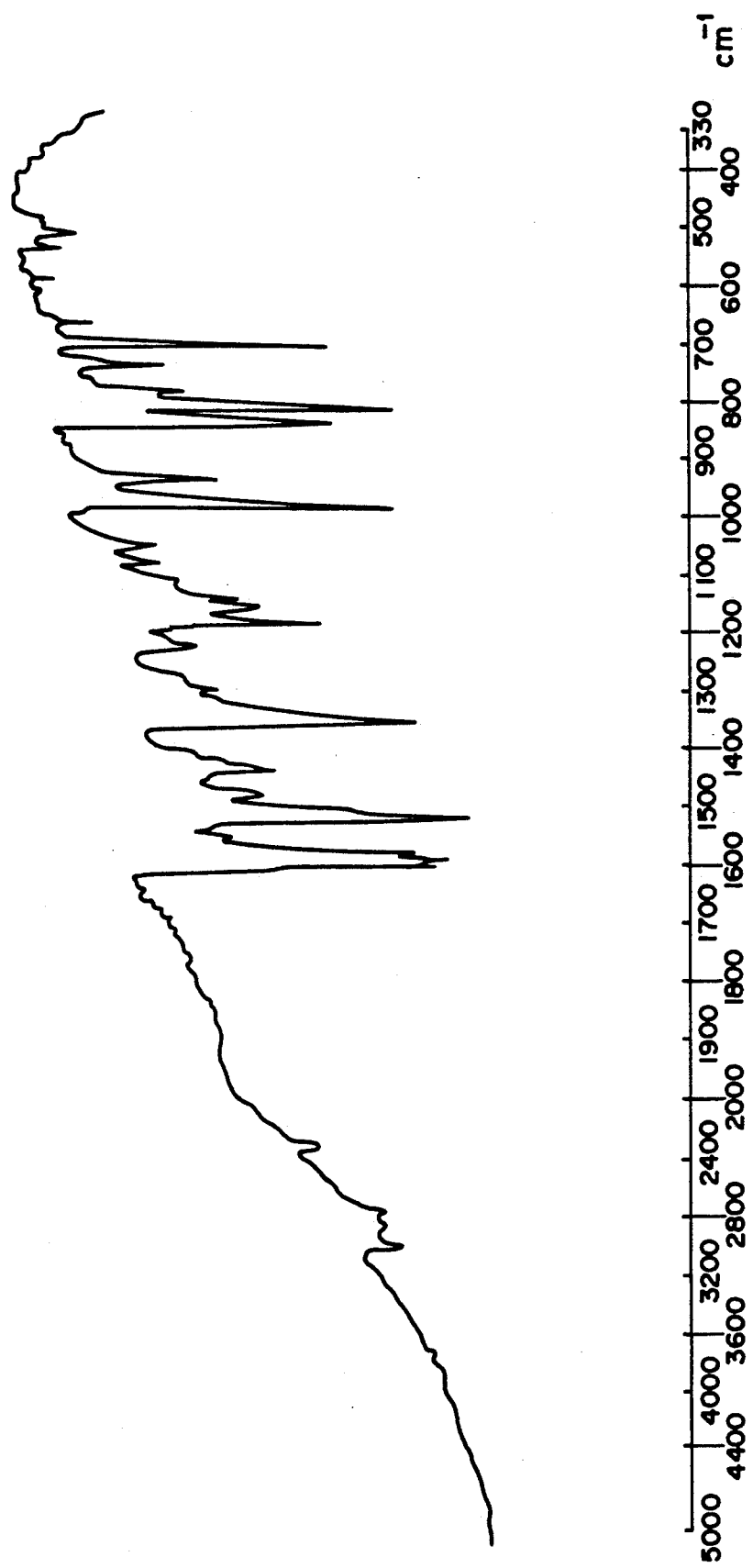
Figure 9:
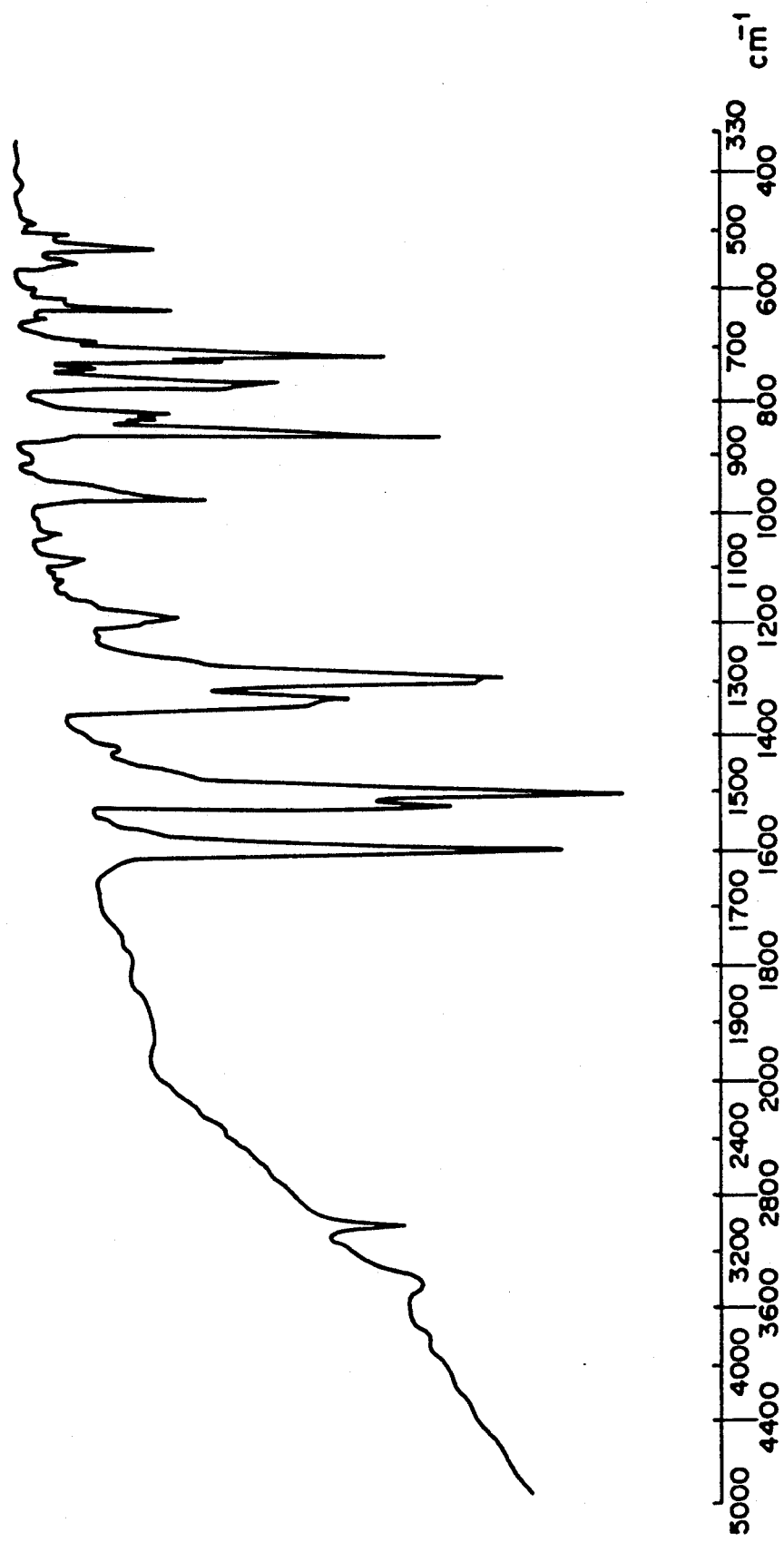

An infrared spectrum was measured by use of a KBr tablet, which is shown in FIG. 7. A characteristic absorption was at 965 cm$^{1}$ ($\delta_{CH,\ trans\text{-}olefin}$).

EXAMPLES 4 to 25

Pyrene-ring-containing olefin compounds Nos. 2, 3, 6, 7, 8, 10, 12, 13, 14, 15, 17, 18, 21, 28, 29, 32, 41, 42, 43, 44, 45 and 46 according to the present invention, which are given in TABLE 2, were prepared in the same manner as in Example 2 by allowing diethyl 1-pyrenylmethylphosphonate to react with the aldehyde compounds given in TABLE 2.

FIG. 2 to FIG. 6, FIG. 8, FIG. 9 and FIG. 11 respectively show the infrared spectra of the pyrene-ring-containing olefin compounds Nos. 2, 3, 6, 7, 10, 17, 18 and 21, which were measured by use of a KBr tablet.

TABLE 2

| Example No. | Aldehyde Compound | Olefin Compound | m.p. (°C.) | Elemental Analysis (%) Found/Calculated | | |
|---|---|---|---|---|---|---|
| | | | | C | H | N |
| 4 | OHC–C₆H₄–N(–C₆H₄–CH₃)₂ | No. 2 | 228.8~300.5 | 91.24/91.35 | 5.65/5.85 | 2.66/2.80 |
| 5 | OHC–C₆H₄–N(–C₆H₄–OCH₃)₂ | No. 3 | 159.7~160.5 | 85.88/85.85 | 5.26/5.50 | 2.63/2.63 |
| 6 | OHC–C₆H₄–N(C₂H₅)(C₆H₅) | No. 6 | 121.5~122.5 | 90.93/90.73 | 5.82/5.86 | 3.25/3.31 |

TABLE 2-continued

| Example No. | Aldehyde Compound | Olefin Compound | m.p. (°C.) | Elemental Analysis (%) Found/Calculated | | |
|---|---|---|---|---|---|---|
| | | | | C | H | N |
| 7 | (aldehyde structure with N-phenyl, N-(4-methoxyphenyl), 4-CHO-phenyl) | No. 7 | 161.0~162.0 | 88.72/88.58 | 5.27/5.44 | 2.75/2.79 |
| 8 | (aldehyde structure with N,N-dibenzyl, 4-CHO-phenyl) | No. 8 | 187.0~188.0 | 91.51/91.33 | 5.63/5.86 | 2.75/2.80 |
| 9 | (aldehyde structure with N-phenyl, N-(4-methylphenyl), 4-CHO-phenyl) | No. 10 | 172.5~173.0 | 91.79/91.50 | 5.47/5.62 | 2.75/2.88 |

TABLE 2-continued

| Example No. | Aldehyde Compound | Olefin Compound | m.p. (°C.) | Elemental Analysis (%) Found/Calculated | | |
|---|---|---|---|---|---|---|
| | | | | C | H | N |
| 10 | OHC–C₆H₄–N(C₂H₅)₂ | pyrenyl–CH=CH–C₆H₄–N(C₂H₅)₂ No. 12 | 149.5~150.3 | 89.71/89.56 | 6.71/6.71 | 3.65/3.73 |
| 11 | OHC–C₆H₅ | pyrenyl–CH=CH–C₆H₅ No. 13 | 154.5~155.5 | 94.83/94.70 | 5.13/5.30 | — |
| 12 | OHC–C₆H₄–CH₃ | pyrenyl–CH=CH–C₆H₄–CH₃ No. 14 | 152.7~153.5 | 94.45/94.30 | 5.53/5.70 | — |
| 13 | OHC–C₆H₄–OCH₃ | pyrenyl–CH=CH–C₆H₄–OCH₃ No. 15 | 158.0~158.5 | 89.95/89.79 | 5.24/5.43 | — |

TABLE 2-continued

| Example No. | Aldehyde Compound | Olefin Compound | m.p. (°C.) | Elemental Analysis (%) Found/Calculated | | |
|---|---|---|---|---|---|---|
| | | | | C | H | N |
| 14 | OHC—CH=CH—⟨C₆H₄⟩—N(CH₃)₂ | ⟨pyrenyl⟩—CH=CH—CH=CH—⟨C₆H₄⟩—N(CH₃)₂ No. 17 | 195~200 | 89.90/90.04 | 5.99/6.21 | 3.78/3.75 |
| 15 | OHC—⟨C₆H₄⟩—N(⟨C₆H₅⟩)₂ | ⟨pyrenyl⟩—CH=CH—⟨C₆H₄⟩—N(⟨C₆H₅⟩)₂ No. 18 | 186.0~187.0 | 91.71/91.68 | 5.20/5.35 | 2.95/2.97 |
| 16 | ⟨pyrenyl⟩—CHO | ⟨pyrenyl⟩—CH=CH—⟨pyrenyl⟩ No. 21 | >300 | 95.42/95.30 | 4.41/4.70 | — |
| 17 | OHC—⟨C₆H₄⟩—CN | ⟨pyrenyl⟩—CH=CH—⟨C₆H₄⟩—CN No. 28 | 193.5~194.5 | 91.25/91.16 | 4.37/4.59 | 4.22/4.25 |

TABLE 2-continued
| Example No. | Aldehyde Compound | Olefin Compound | m.p. (°C.) | Elemental Analysis (%) Found/Calculated | | |
|---|---|---|---|---|---|---|
| | | | | C | H | N |
| 18 | 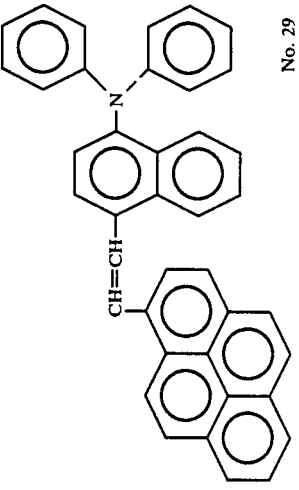 | 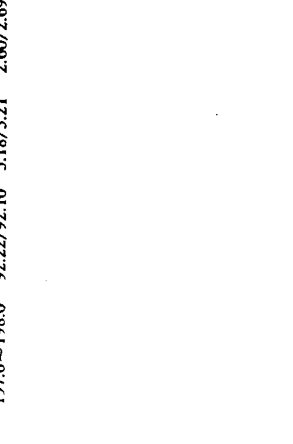 No. 29 | 197.0~198.0 | 92.22/92.10 | 5.18/5.21 | 2.60/2.69 |
| 19 | 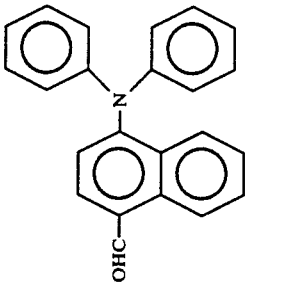 | 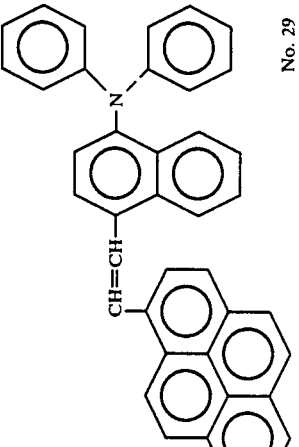 No. 32 | 229.5~230.5 | 90.73/90.59 | 5.00/5.24 | — |
| 20 | 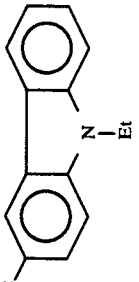 | 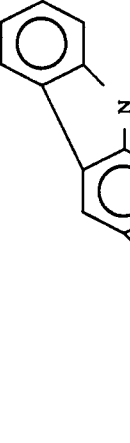 No. 41 | 202.0~203.0 | — | — | — |

TABLE 2-continued

| Example No. | Aldehyde Compound | Olefin Compound | m.p. (°C.) | Elemental Analysis (%) Found/Calculated | | |
|---|---|---|---|---|---|---|
| | | | | C | H | N |
| 21 | Me₂N—C₆H₄—CH=CH—CHO | pyrenyl-CH=CH—CH=CH—C₆H₄—NMe₂ (No. 42) | 198~200 | — | — | — |
| 22 | 2-OCH₃, 1-OHC naphthalene | pyrenyl-CH=CH-(2-OCH₃-naphth-1-yl) (No. 43) | 220.5~221.0 | 90.77/90.59 | 5.03/5.24 | — |
| 23 | 4-N(CH₃)₂, 3-Cl, 1-OHC benzene | pyrenyl-CH=CH-(4-N(CH₃)₂-3-Cl-phenyl) (No. 44) | 173.0~174.0 | 81.91/81.76 | 5.12/5.29 | 3.60/3.67 |

TABLE 2-continued

| Example No. | Aldehyde Compound | Olefin Compound | m.p. (°C.) | Elemental Analysis (%) Found/Calculated | | |
|---|---|---|---|---|---|---|
| | | | | C | H | N |
| 24 | OHC—CH=CH—(C₆H₄)—OCH₃ | CH=CH—CH=CH—(pyrene), with phenyl-OCH₃ (No. 45) | 173.0~174.0 | 90.18/89.96 | 5.42/5.60 | — |
| 25 | OHC—C(CH₃)=CH—(C₆H₅) | CH=CH—C(CH₃)=CH—(pyrene), with phenyl (No. 46) | 145.0~146.0 | 94.40/94.14 | 5.57/5.86 | — |

EXAMPLE 26

Preparation of
1-methyl-1-(p-chlorophenyl)-2-(1-pyrenyl)ethylene)
(Olefin Compound No. 19)

2.47 g (7 mmol) of diethyl 1-pyrenylmethylphosphonate and 1.08 g (7 mmol) of p-chloroacetophenone were dissolved with stirring in 25 ml of N,N-dimethylformamide. To this reaction mixture, 1.24 g (7×1.5 mmol) of potassium tert-butoxide was gradually added over a period of 2 hours. The reaction mixture was then stirred at room temperature for 9 hours, then at 60° C. for 9 hours, neutralized with acetic acid, extracted with toluene. The extract was washed with water, dried over anhydrous magnesium sulfate and concentrated under reduced pressure. Crystals separated out. The crystals were separated by filtration, dried and then purified by column chromatography on a column of silica gel, using a mixed solvent of toluene/n-hexane (1/1) as the eluent, whereby a yellow powder was obtained with a yield of 1.12 g (44.8%).

The thus obtained yellow powder was recrystallized from a mixed solvent of toluene and n-hexane, whereby yellow crystals were obtained. The thus obtained yellow crystals were washed with 100 ml of ethanol with application of heat thereto, whereby pure 1-methyl-(p-chlorophenyl)-2-(1-pyrenyl)ethylene was obtained in the form of yellow crystals. The melting point was 161.6°–163.7° C.

The results of elemental analysis of the 1-methyl-1-(p-chlorophenyl)-2-(1-pyrenyl)ethylene were as follows:

|     | Found | Calculated |
| --- | ----- | ---------- |
| % C | 85.22 | 85.10      |
| % H | 4.65  | 4.86       |

Figure 10:
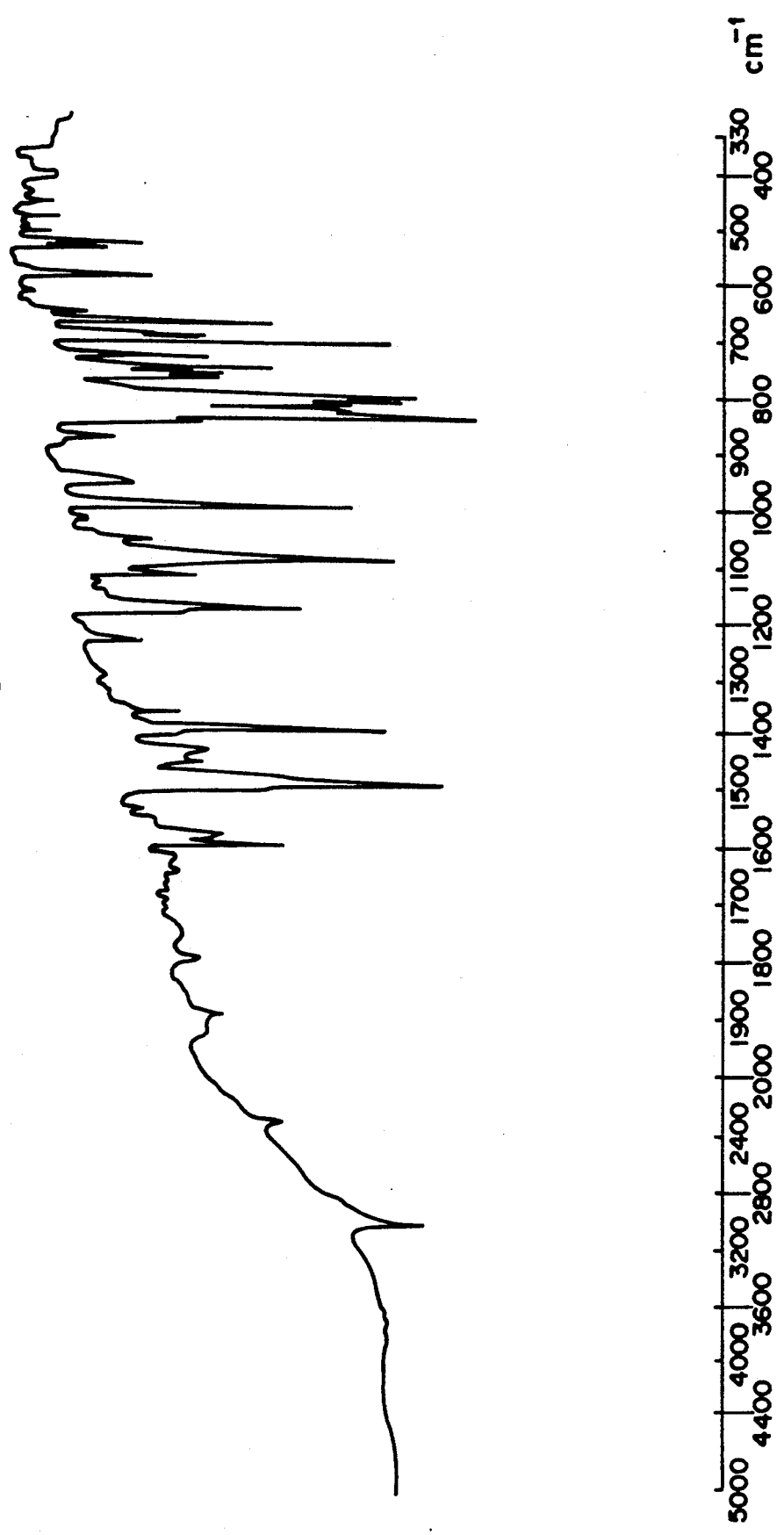
Figure 11:
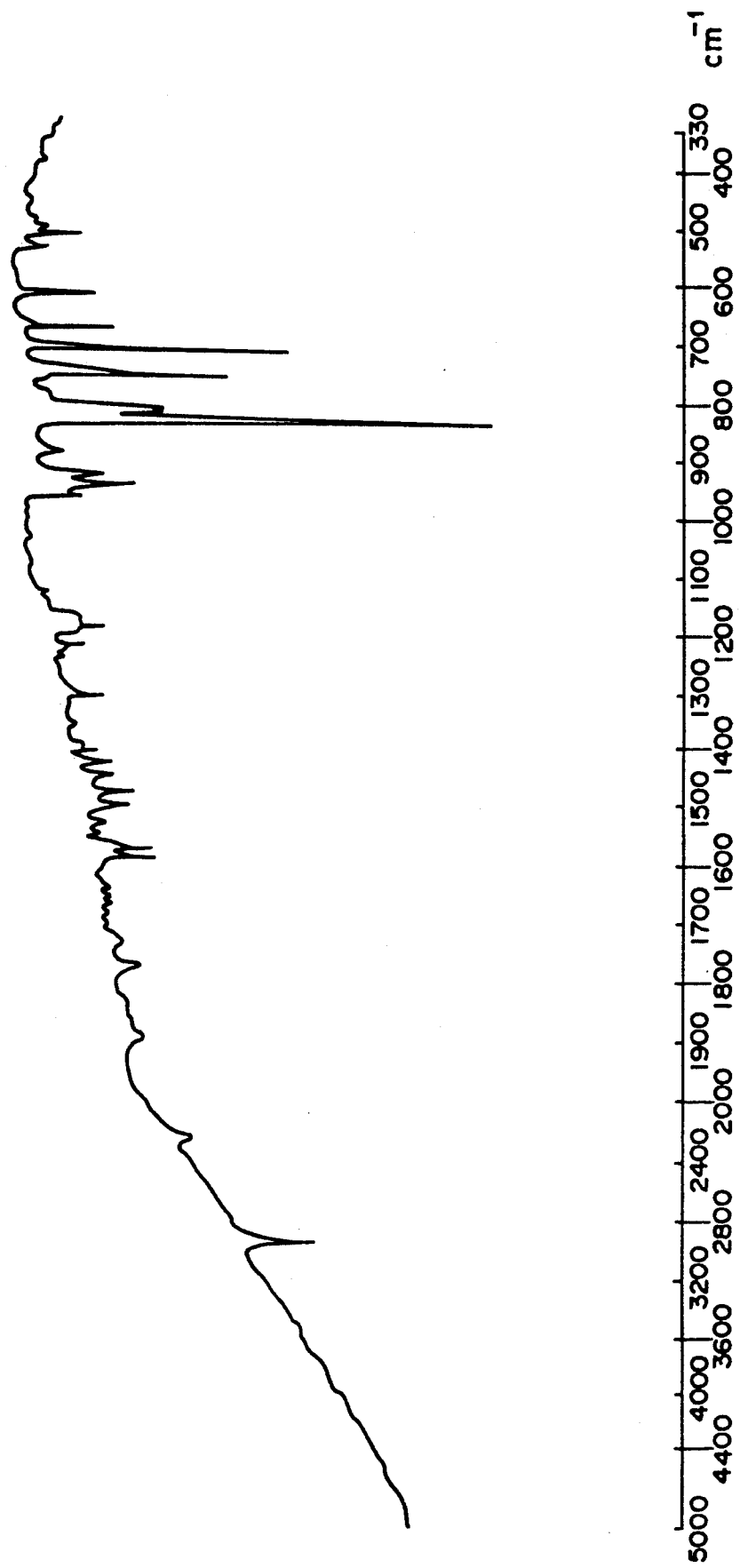

The infrared spectrum thereof measured by use of a KBr tablet is shown in FIG. 10.

EXAMPLE 27

Preparation of β,β'-bis(1-pyrenyl)-1,4-divinylbenzene
(Olefin Compound No. 23)

3.52 g (10 mmol) of diethyl 1-pyrenylmethylphosphonate and 0.67 g (5 mmol) of terephthalaldehyde were dissolved in 30 ml of N,N-dimethylformamide. To this reaction mixture, 1.68 g (15 mmol) of potassium tert-butoxide was added at 22°–29° C. The reaction mixture was then stirred at room temperature for 3 hours and then diluted with 30 ml of methanol. Crystals separated out. The crystals were separated by filtration, washed with water and then with methanol, dried under reduced pressure with application of heat, whereby a yellow powder was obtained with a yield of 2.46 g (92.8%).

The thus obtained yellow powder was recrystallized from N,N-dimethylformamide, whereby β,β'-bis(1-pyrenyl)-1,4-divinylbenzene with the following formula was obtained in the form of yellow leaf-shaped crystals.

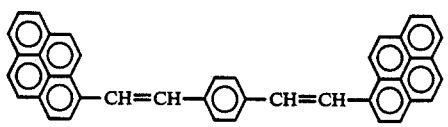

The melting point of the product was 338° C. in terms of DTA endothermic peak temperature.

The results of elemental analysis of the β,β'-bis(1-pyrenyl)-1,4-divinylbenzene were as follows:

|     | Found | Calculated |
| --- | ----- | ---------- |
| % C | 95.33 | 95.05      |
| % H | 4.69  | 4.95       |

Figure 12:
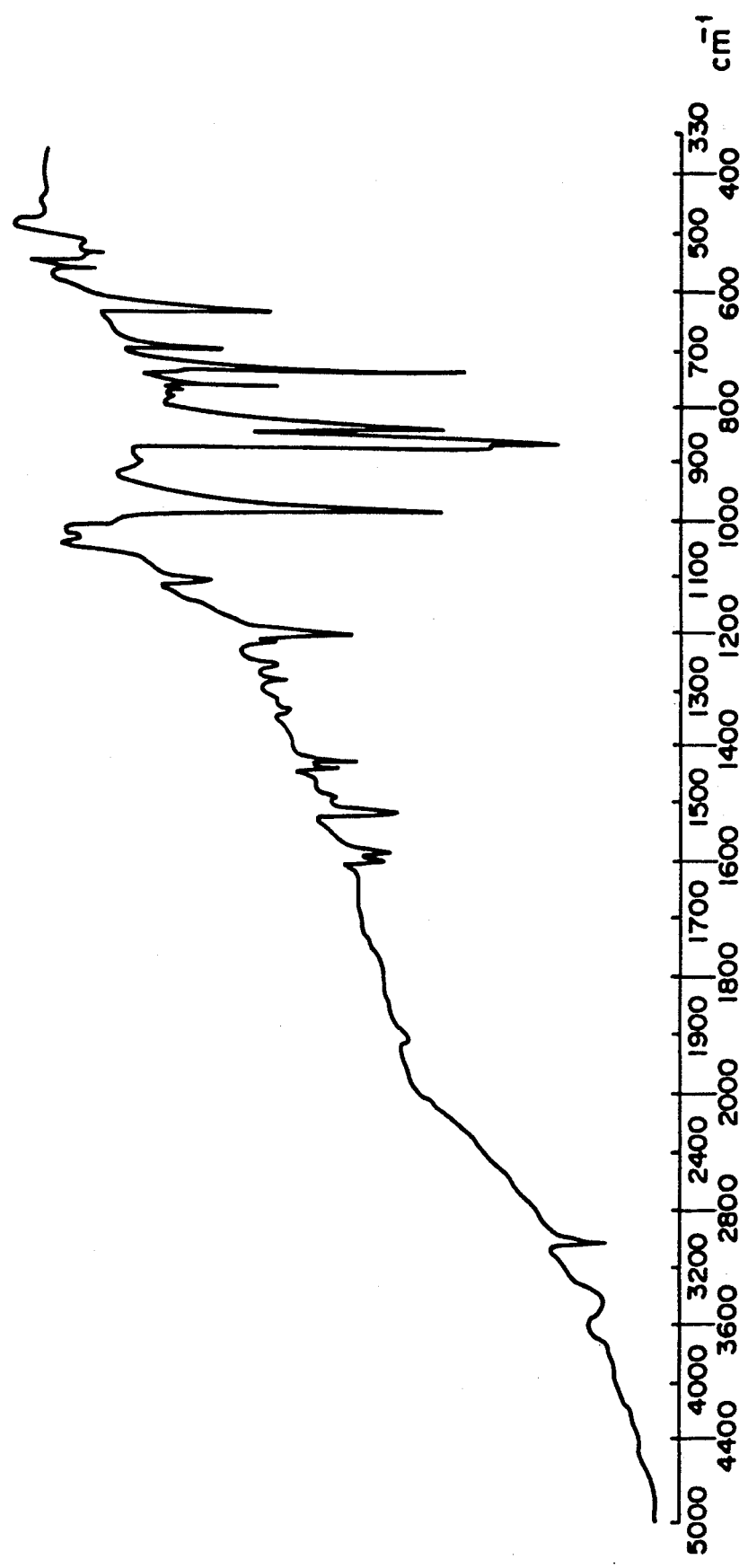

The infrared spectrum thereof measured by use of a KBr tablet is shown in FIG. 12. A characteristic trans-olefin absorption was observed at 965 cm$^{-1}$.

EXAMPLES 28 to 36

Pyrene-ring-containing olefin compounds Nos. 24, 25, 26, 28, 36, 37, 38, 39 and 40 according to the present invention, which are given in TABLE 3, were prepared in the same manner as in Example 26 by allowing diethyl 1-pyrenylmethylphosphonate to react with the aldehyde compounds given in TABLE 3.

TABLE 3

| Example No. | Aldehyde Compound | Olefin Compound | m.p. (°C.) | Elemental Analysis (%) Found/Calculated C | H | N |
|---|---|---|---|---|---|---|
| 28 | (1,3-benzenedicarboxaldehyde) | No. 24 (1,3-bis(2-(pyren-1-yl)vinyl)benzene) | 272.0~273.0 | 95.25/95.05 | 4.70/4.95 | |
| 29 | (1,2-benzenedicarboxaldehyde) | No. 25 | 230.5~231.0 | 94.81/95.05 | 4.70/4.95 | |
| 30 | (2,5-dimethoxyterephthalaldehyde) | No. 26 | 313.0 | 89.26/89.45 | 4.84/5.13 | |

TABLE 3-continued

| Example No. | Aldehyde Compound | Olefin Compound | m.p. (°C.) | Elemental Analysis (%) Found/(Calculated) | | |
|---|---|---|---|---|---|---|
| | | | | C | H | N |
| 31 | 4-CN-C6H4-COCH3 (H3COC-C6H4-CN) | No. 28 (pyrene-CH=C(CH3)-C6H4-CN, para) | a) 148.0 | 91.00 (90.92) | 4.73 (5.00) | 4.05 (4.08) |
| 32 | 3-CN-C6H4-CHO | No. 36 (pyrene-CH=CH-C6H4-CN, meta) | 183.0~183.5 | 91.39 (91.15) | 4.50 (4.60) | 4.18 (4.25) |
| 33 | 2-CN-C6H4-CHO | No. 37 (pyrene-CH=CH-C6H4-CN, ortho) | 178.5~179.0 | 91.32 (91.15) | 4.51 (4.60) | 4.17 (4.25) |

TABLE 3-continued

| Example No. | Aldehyde Compound | Olefin Compound | m.p. (°C.) | Elemental Analysis (%) Found/(Calculated) | | |
|---|---|---|---|---|---|---|
| | | | | C | H | N |
| 34 | 4-SCH₃-C₆H₄-CHO | Pyrene-CH=CH-C₆H₄-SCH₃ (No. 38) | 165.0~165.5 | 87.78 (85.67) | 5.12 (5.19) | 9.08 (9.15) |
| 35 | Phenanthrene-CHO | Pyrene-CH=C-Phenanthrene (No. 39) | 228~228.5 | 95.13 (95.01) | 4.87 (4.99) | — |
| 36 | 4-COOCH₃-C₆H₄-CHO | Pyrene-CH=CH-C₆H₄-COOCH₃ (No. 40) | 184~184.5 | 86.25 (86.15) | 4.81 (5.02) | 8.79 (8.83) | a) TG-DTA Endothermic Peak Temperature

EXAMPLES 37

76 parts by weight of Diane Blue (C.I. Pigment Blue 25, C.I. 21180) serving as a charge generating material, 1260 parts by weight of a 2% tetrahydrofuran solution of a polyester resin (Trademark "Vylon 200" made by Toyobo Company, Ltd.) and 3700 parts by weight of tetrahydrofuran were dispersed and ground in a ball mill pot. The thus prepared dispersion was coated on an aluminum surface of an aluminum-deposited polyester film by a doctor blade, and then dried at room temperature, so that a charge generation layer having a thickness of about 1 μm was formed on the aluminum-deposited polyester film.

2 parts by weight of pyrene-ring-containing olefin compound No. 1 in Table 1, and 2 parts by weight of polycarbonate resin (Trademark "Panlite K-1300" made by Teijin Limited) were dissolved in 16 parts by weight of tetrahydrofuran to prepare a solution. The resulting solution was coated on the above formed charge generation layer by a doctor blade, and dried at 80° C. for 2 minutes and then at 120° C. for 5 minutes, so that a charge transport layer having a thickness of about 20 μm was formed on the charge generation layer. Thus a two-layered type electrophotographic photoconductor No. 1 according to the present invention was prepared.

EXAMPLES 38 to 69

The procedure for Example 1 was repeated except that the Diane Blue serving as a charge generating material and the pyrene-ring-containing olefin compound No. 1 serving as a charge transporting material employed in Example 1 were replaced by the respective charge generating materials and charge transporting materials listed in the following TABLE 4, whereby two-layered type electrophotographic photoconductors No. 2 to No. 33 according to the present invention were prepared.

TABLE 4

| Photoconductor No. | Charge Generating Material | Charge Transporting Material (Olefin Compound No.) |
|---|---|---|
| 1 | (azo compound with two naphthol-CONHPh groups linked via biphenyl with two OCH₃ groups and N=N bonds) | 1 |
| 2 | (azo compound with two naphthol-CONHPh groups linked via biphenyl with two Cl groups and N=N bonds) | 1 |
| 3 | (azo compound with two naphthol-CONH(2,4-dimethylphenyl) groups linked via distyrylbenzene system with N=N bonds) (hereinafter referred to as P-1) | 1 |

TABLE 4-continued

| Photo-conductor No. | Charge Generating Material | Charge Transporting Material (Olefin Compound No.) |
|---|---|---|
| 4 | (bisazo naphthol compound with two phenyl carbamoyl groups linked via -N=N-C₆H₄-C(=O)-O-C(=O)-C₆H₄-N=N-) | 1 |
| 5 | (bisazo naphthol compound with two 2-chlorophenyl carbamoyl groups linked via -N=N-naphthyl-C(=O)-fluorenyl-naphthyl-N=N-) | 1 |
| 6 | (polymeric trisazo compound, hereinafter referred to as P-2) | 1 |

TABLE 4-continued

| Photo-conductor No. | Charge Generating Material | Charge Transporting Material (Olefin Compound No.) |
|---|---|---|
| 7 | (hereinafter referred to as P-3) β-type Copper Phthalocyanine | 1 |
| 8 |  | 2 |
| 9 |  | 2 |
| 10 | P-1 | 2 |
| 11 | P-2 | 2 |
| 12 | P-3 | 2 |
| 13 | P-1 | 3 |
| 14 | P-2 | 3 |
| 15 | P-3 | 3 |
| 16 | P-1 | 15 |
| 17 | P-2 | 15 |
| 18 | P-3 | 15 |
| 19 | P-1 | 13 |
| 20 | P-2 | 13 |
| 21 | P-3 | 13 |
| 22 | P-1 | 10 |
| 23 | P-2 | 10 |
| 24 | P-3 | 10 |
| 25 | P-1 | 7 |
| 26 | P-2 | 7 |
| 27 | P-3 | 7 |
| 28 | P-1 | 20 |

TABLE 4-continued

| Photo-conductor No. | Charge Generating Material | Charge Transporting Material (Olefin Compound No.) |
|---|---|---|
| 29 | P-2 | 20 |
| 30 | P-3 | 20 |
| 31 | P-1 | 18 |
| 32 | P-2 | 18 |
| 33 | P-3 | 18 |

EXAMPLE 70

Selenium was vacuum-deposited on an aluminum plate having a thickness of about 300 μm which serves as an electroconductive substrate, so that a charge generation layer having a thickness of about 1 μm was formed on the aluminum plate.

2 parts by weight of pyrene-ring-containing olefin compound No. 1 in Table 1, 3 parts by weight of polyester resin (Trademark "Polyester Adhesive 49000" made by Du Pont de Nemours, E. I. & Co.) were dissolved in 45 parts by weight of tetrahydrofuran. The resulting solution was coated on the above formed charge generation layer by a doctor blade, dried at room temperature, and then dried under reduced pressure, so that a charge transport layer having a thickness of about 10 μm was formed on the charge generation layer. Thus a two-layered type electrophotographic photoconductor No. 34 according to the present invention was prepared.

EXAMPLE 71

A perylene pigment having the following formula was vacuum-deposited on an aluminum plate having a thickness of about 300 μm, so that a charge generation layer having a thickness of about 0.6 μm was formed on the aluminum plate:

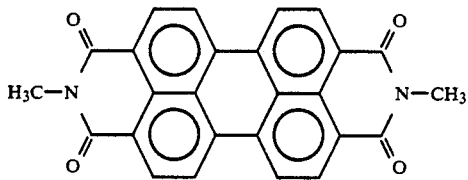

2 parts by weight of pyrene-ring-containing olefin compound No. 1 in Table 1, and 3 parts by weight of a polyester resin (Trademark "Polyester Adhesive 49000" made by Du Pont de Nemours, E. L. & Co.) were dissolved in 45 parts by weight of tetrahydrofuran. The resulting solution was coated on the above formed charge generation layer by a doctor blade, dried at room temperature, and then dried under reduced pressure, so that a charge transport layer having a thickness of about 10 μm was formed on the charge generation layer. Thus a two-layered type electrophotographic photoconductor No. 34 according to the present invention was prepared.

EXAMPLE 72

A mixture of 1 part by weight of the same Diane Blue as employed in Example 1 and 158 parts by weight of tetra-hydrofuran was dispersed and ground in a ball mill pot to prepare a dispersion. To the thus prepared dispersion, 12 parts by weight of pyrene-ring-containing olefin compound No. 1 in Table 1 and 18 parts by weight of polyester resin (Trademark "Polyester Adhesive 49000" made by Du Pont de Nemours, E. I. & Co.) were added to prepare a solution. The resulting solution was coated on an aluminum-deposited polyester film by a doctor blade, and dried at 100° C. for 30 minutes, so that a photoconductive layer having a thickness of about 16 μm was formed on the electroconductive support. Thus, an electrophotographic photoconductor No. 36 according to the present invention was prepared

EXAMPLE 37

The solution for forming a charge transport layer, prepared in Example 1, was coated on an aluminum-deposited polyester film by a doctor blade, and dried at 80° C. for 2 minutes and then at 120° C. for 5 minutes, so that a charge transport layer having a thickness of about 20 μm was formed on the aluminum-deposited polyester film.

A mixture of 13.5 parts by weight of bisazo pigment (P-2), 5.4 parts by weight of polyvinyl butyral (Trademark "XYHL" made by Union Carbide Japan K. K.), 680 parts by weight of tetrahydrofuran and 1020 parts by weight of ethyl cellosolve was dispersed and ground in a ball mill pot. To this dispersion, 1700 parts by weight of ethyl cellosolve was further added to prepare a solution The resulting was coated on the above formed charge transport layer by spray coating and dried at 100° C. for 10 minutes, so that a charge generation layer having a thickness of about 0.2 μm was formed on the charge transport layer.

A mixed solution of methanol and n-butanol containing a polyamide resin [Trademark "CM-8000" made by Toray Silicone Co., Ltd.) was coated on the above formed charge generation layer by spray coating and dried at 120° C. for 30 minutes, so that a protective layer having a thickness of about 0.5 μm was formed on the charge generation layer. Thus, a two-layered type electrophotographic photoconductor No. 37 according to the present invention was prepared Each of the above-prepared electrophotographic photoconductors No. 1 through No. 37 according to the present invention was charged negatively or positively in the dark under application of −6 kV or +6 kV of corona charge for 20 seconds, using a commercially available electrostatic copying sheet testing apparatus ("Paper Analyzer Model SP-428" made by Kawaguchi Electro Works Co., Ltd.). Then, each electrophotographic photoconductor was allowed to stand in the dark for 20 seconds without applying any charge thereto, and the surface potential Vpo (V) of the photoconductor was measured. The photoconductor was then illuminated by a tungsten lamp in such a manner that the illuminance on the illuminated surface of the photoconductor was 4.5 lux, and the exposure $E_{\frac{1}{2}}$ (lux.-sec) required to reduce the initial surface potential Vpo (V) to ½ the initial surface potential Vpo (V) was measured The results are shown in TABLE 5.

TABLE 5

| Photoconductor No. | Vpo (V) | $E_{\frac{1}{2}}$ (lux · sec) |
|---|---|---|
| 1 | −1130 | 1.50 |
| 2 | −1070 | 1.31 |
| 3 | −1150 | 0.96 |
| 4 | −1350 | 1.48 |
| 5 | −1121 | 0.89 |
| 6 | −1070 | 0.42 |
| 7 | −1180 | 1.75 |
| 8 | −1240 | 1.52 |
| 9 | −1120 | 1.13 |
| 10 | −1120 | 0.92 |
| 11 | −1010 | 0.67 |
| 12 | −850 | 0.39 |
| 13 | −1050 | 0.88 |
| 14 | −677 | 0.60 |
| 15 | −478 | 0.36 |
| 16 | −1050 | 1.40 |
| 17 | −1099 | 1.20 |
| 18 | −680 | 0.95 |
| 19 | −1320 | 2.60 |
| 20 | −1354 | 2.50 |

TABLE 5-continued

| Photoconductor No. | Vpo (V) | E₁ (lux · sec) |
|---|---|---|
| 21 | −950 | 1.97 |
| 22 | −1160 | 0.92 |
| 23 | −1120 | 0.87 |
| 24 | −1030 | 0.39 |
| 25 | −1100 | 0.89 |
| 26 | −850 | 0.75 |
| 27 | −950 | 0.37 |
| 28 | −1180 | 0.91 |
| 29 | −1120 | 0.81 |
| 30 | −1120 | 0.65 |
| 31 | −1160 | 0.93 |
| 32 | −1015 | 0.87 |
| 33 | −980 | 0.42 |
| 34 | −920 | 1.95 |
| 35 | −1190 | 3.50 |
| 36 | +1280 | 1.65 |
| 37 | +1275 | 0.98 |

Each of the above-mentioned electrophotographic photoconductors according to the present invention was incorporated in a commercially available electrophotographic copying machine and charged negatively or positively. Then it was exposed to the light through an original to form a latent electrostatic image on the surface of the photoconductor. The thus formed latent electrostatic image was developed by a dry-type developer to a visible image The resulting visible image was transferred to a sheet of plain paper and fixed thereon, so that a clear transferred image was formed. In the case where a wet-type developer was employed, a clear image was formed likewise.

COMPARATIVE EXAMPLE 1

Example 1 was repeated except that the charge generating material used in Example 1 was replaced by a charge generating material P-2 shown in TABLE 4, and the olefin compound No. 1 used as the charge transporting material in Example 1 was replaced by 4,4',4"-trimethyltriphenyl amine, whereby a comparative electrophotographic photoconductor was prepared.

The electrophotographic photoconductor thus obtained was evaluated in the same manner as described above, and $V_{po}$ and $E_{178}$ were measured. In addition, the residual potential (Vr) 30 seconds after illumination was also measured.

The results are shown in TABLE 6 along with the data with respect to electrophotographic photoconductor No. 5 according to the present invention for comparison.

TABLE 6

|  | $V_{po}$ | $E_{\frac{1}{2}}$ | Vr |
|---|---|---|---|
| Photoconductor No. 5 | −1121 | 0.80 | 0 |
| Comp. Photoconductor | −1287 | 1.24 | −129 |

The above data demonstrate that the electrophotographic photoconductor No. 5 according to the present invention has a higher photosensitivity, indicated by $E_{\frac{1}{2}}$, in comparison with the comparative photoconductor, and has no residual potential Vr.

The electrophotographic photoconductors according to the present invention are excellent in the photoconductive characteristics. Moreover, they are thermally and mechanically stable, and can be produced inexpensively.

What is claimed is:

1. An electrophotographic photoconductor comprising an electroconductive support and a photoconductive layer formed thereon comprising a charge generation layer containing a charge generating material and a charge transport layer containing a binder and a pyrene-ring-containing olefin compound having formula (I):

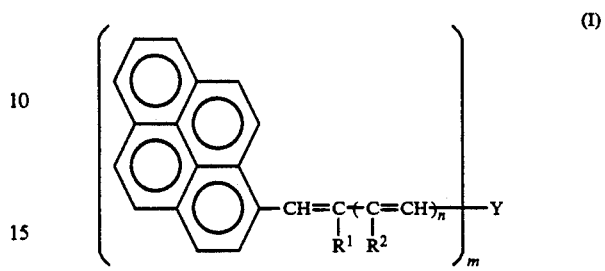

wherein $R^1$ and $R^2$ each represent hydrogen or an alkyl group which may have a substituent; Y is an aliphatic hydrocarbon group which may have a substituent, a cyclic hydrocarbon group which may have a substituent, or an aromatic group which may have a substituent, said aromatic group being selected from the group consisting of a phenyl group, a biphenyl group, a terphenyl group, a pentalenyl group, an indenyl group, a naphthyl group, an azulenyl group, a heptalenyl group, an asindacenyl group, a fluorenyl group, an s-indacenyl group, an acenaphthylenyl group, a pleiadenyl group, an acenaphthenyl group, a phenalenyl group, a phenanthrenyl group, an anthracenyl group, an acephenanthrenyl group, an aceanthrylenyl group, a triphenylenyl group, a pyrenyl group, a chrysenyl group, a naphthacenyl group, a thienyl group, a furyl group, a 2-pyridyl group, 4-pyridyl group, a 3-indolyl group, a 2-thinolynyl group, a 3,4-benzpyranyl group, an acridinyl group, a thiazolyl group, a benzthiazolonyl group, a 9-methylcarbazolyl group, a 9-propylcarbazolyl group, a 9-phenylcarbazolyl group and a 9-tolylcarbazolyl group; said substituent being selected from the group consisting of a halogen atom, cyano group, a nitro group, an alkyl group having 1 to 12 carbon atoms, an alkoxyl group having 1 to 12 carbon atoms, an aryloxy group, an alkylmercapto group having 1 to 12 carbon atoms and a

group, wherein $R^5$ and $R^3$ each represent hydrogen, an alkyl group having 1 to 12 carbon atoms or an aryl group; said alkyl group, said alkoxyl group and said alkylmercapto group may further include a fluorine atom, a hydroxyl group, a cyano group, an alkoxyl group having 1 to 4 carbon atoms or a phenyl group; said aryl group, said aryloxy group and said phenyl group may be substituted with a halogen atom, an alkyl group having 1 to 4 carbon atoms, or an alkoxyl group having 1 to 4 carbon atoms; n is an integer of 0 or 1; and m is an integer of 1 to 3; provided that when n is 0 and m is 1, $R^1$ is hydrogen and Y is an aromatic group with a substituent

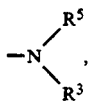

$R^5$ and $R^3$ each represent hydrogen, and Y and $R^1$ may be bonded to form a ring.

2. The electrophotographic photoconductor as claimed in claim 38, wherein said aromatic group represented by Y is a non-fused carbon cyclic aromatic group.

3. The electrophotographic photoconductor as claimed in claim 1, wherein said aromatic group represented by Y is a fused polycyclic hydrocarbon group.

4. The electrophotographic photoconductor as claimed in claim 1, wherein said aromatic group represented by Y is a heterocyclic aromatic group.

5. The electrophotographic photoconductor as claimed in claim 2, wherein said non-fused carbon cyclic aromatic group is selected from the group consisting of phenyl group, biphenyl group and terphenyl group.

6. The electrophotographic photoconductor as claimed in claim 3, wherein said fused polycyclic hydrocarbon group is selected from the group consisting of pentalenyl group, indenyl group, naphthyl group, azulenyl group, heptalenyl group, biphenyl group, as-indacenyl group, fluorenyl group, fluorenyl group, s-indacenyl group, acena-phthylenyl group, pleiadenyl group, acenaphthenyl group, phenalenyl group, phenanthrenyl group, anthracenyl group, acephenanthrenyl group, aceanthrylenyl group, triphenylenyl group, pyrenyl group, chrysenyl group, and naphthacenyl group.

7. The electrophotographic photoconductor as claimed in claim 4, wherein said heterocyclic aromatic group is selected from the group consisting of thienyl group, furyl group, 2-pyridyl group, 4-pyridyl group, 3-indolyl group, 2-thinolynyl group, 3,4-benzpyranyl group, acridinyl group, thiazolyl group, benzthiazolonyl group, 9-methylcarbazolyl group, 9-propylcarbazolyl group, 9-phenylcarbazolyl group, 9-tolylcarbazolyl group.

8. The electrophotographic photoconductor as claimed in claim 38, wherein said aromatic group represented by Y has a substituent selected from the group consisting of halogen, cyano group, nitro group, alkyl group having 1 to 12 carbon atoms which may have a substituent, alkoxyl group, aryloxy group, alkylmercapto group, amino group represented by

in which $R^5$ and $R^3$ each represent hydrogen or alkyl group having 1 to 12 carbon atoms, alkylenedioxy group and alkylenedithio group.

9. The electrophotographic photoconductor as claimed in claim 8, wherein said alkyl group is selected from the group consisting of methyl group, ethyl group, n-propyl group, i-propyl group, t-butyl group, s-butyl group, n-butyl group, i-butyl group, trifluoromethyl group, 2-hydroxyethyl group, 2-cyanoethyl group, 2-ethoxyethyl group, 2-methoxyethyl group, benzyl group, 4-chlorobenzyl group, 4-methylbenzyl group, 4-methoxybenzyl group and 4-phenylbenzyl group.

10. The electrophotographic photoconductor as claimed in claim 8, wherein said alkoxyl group is selected from the group consisting of methoxy group, ethoxy group, n-propoxy group, i-propoxy group, t-butoxy group, n-butoxy group, s-butoxy group, i-butoxy group, 2-hydroxyethoxy group, 2-cyanoethoxy group, benzyloxy group, 4-methylbenzyloxy group, and trifluoromethoxy group.

11. The electrophotographic photoconductor as claimed in claim 8, wherein said aryloxy group is selected from the group consisting of phenoxy group, 1-naphthyloxy group, 2-naphthyloxy group, 4-methylphenoxy group, 4-methoxyphenoxy group, 4-chlorophenoxy group, and 6-methyl-2-naphthyloxy group.

12. The electrophotographic photoconductor as claimed in claim 8, wherein said alkylmercapto group is selected from the group consisting of methylthio group, ethylthio group, phenylthio group, and p-methylphenylthio group.

13. The electrophotographic photoconductor as claimed in claim 8, wherein said amino group is selected from the group consisting of amino group, diethylamino group, diethylamino group, N-methyl-N-phenylamino group, N,N-diphenylamino group, N,N-di(p-tolyl)amino group, dibenzylamino group, pyperidino group, morpholino group, and juloridyl group.

14. The electrophotographic photoconductor as claimed in claim 8, wherein said alkylenedioxy group is methylene dioxy group.

15. The electrophotographic photoconductor as claimed in claim 8, wherein said alkylenedithio group is methylene dithio group.

16. The electrophotographic photoconductor as claimed in claim 1, wherein said photoconductive layer comprises a charge generating material and a charge transporting medium comprising said pyrene-ring-containing compound and a binder agent, in which said charge generating material is dispersed.

17. The electrophotographic photoconductor as claimed in claim 1, wherein the amount of said pyrene-ring-containing compound is in the range of 30 to 70 wt.% of the entire weight of said photoconductive layer.

18. The electrophotographic photoconductor as claimed in claim 16, wherein the amount of said pyrene-ring-containing compound is in the range of 10 wt.% to 95 wt.% of the entire weight of said photoconductive layer, and the amount of the said charge generating material is in the range of 0.1 wt.% to 50 wt.% of the entire weight of said photoconductive layer.

19. The electrophotographic photoconductor as claimed in claim 1, wherein the amount of the said charge generating material is in the range of 10 wt.% to 95 wt.% of the entire weight of said charge generation layer, and the amount of said pyrene-ring-containing compound is in the range of 10 wt.% to 95 wt.% of the entire weight of said charge transport layer.

20. The electrophotographic photoconductor of claim 1, wherein said photoconductive layer further comprises a sensitizing dye.

21. The electrophotographic photoconductor of claim 20, wherein said sensitizing dye is present in said photoconductive layer in an amount in the range of from 0.1 to 5 wt.%.

22. The electrophotographic photoconductor of claim 1, wherein said binder is a condensation resin selected from the group consisting of polyamides, polyurethanes, polyesters, epoxy resins, polyketones and polycarbonates, or a vinyl copolymer selected from the group consisting of polyvinylketones, polystyrene, poly-N-vinylcarbazole and polyacrylamide.

* * * * *

UNITED STATES PATENT AND TRADEMARK OFFICE
CERTIFICATE OF CORRECTION

PATENT NO. : 5,268,246
DATED : DECEMBER 7, 1993
INVENTOR(S) : TAMOTSU ARUGA ET AL

It is certified that error appears in the above-identified patent and that said Letters Patent is hereby corrected as shown below:

Column 2, line 9, "7-10735" should read --47-10735--.

Column 4, line 20, "formula III] in" should read --formula [III] in--.

Column 6, line 8, "These alkyl group may" should read --These alkyl groups may--.

line 60, "aryl group may" should read --aryl groups may--.

Column 7, under Table 1, lines 13-19,

"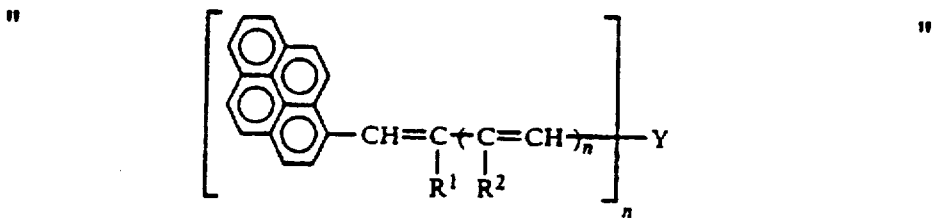"

should read

--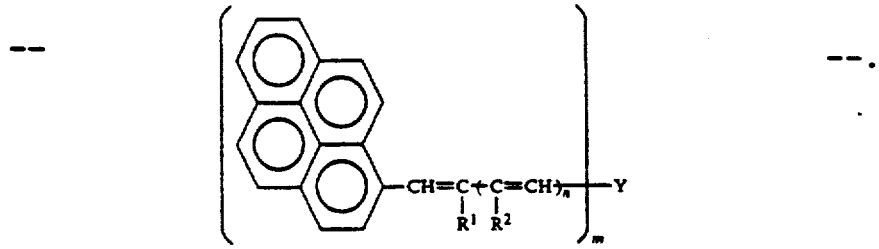--.

UNITED STATES PATENT AND TRADEMARK OFFICE
CERTIFICATE OF CORRECTION

PATENT NO. : 5,268,246

DATED : DECEMBER 7, 1993

INVENTOR(S) : TAMOTSU ARUGA ET AL

It is certified that error appears in the above-identified patent and that said Letters Patent is hereby corrected as shown below:

Column 8, under Table 1-continued, lines 3-8,

"
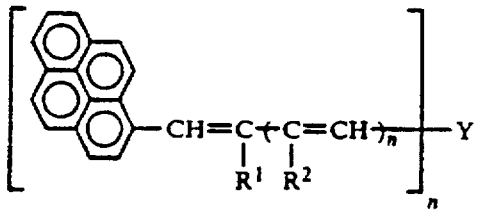
"

should read

--
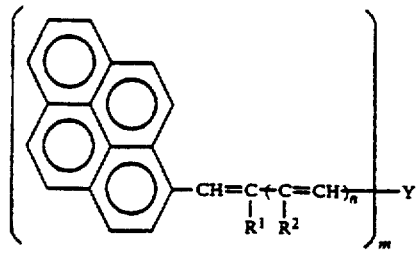
--.

Column 9, under Table 1-continued, lines 3-8,

"
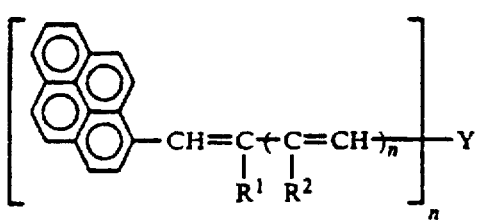
"

should read

--
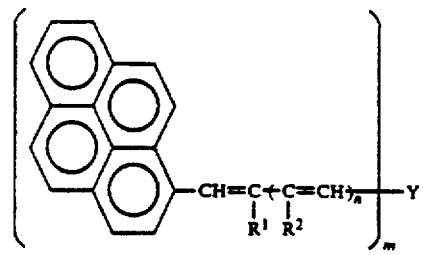
--.

UNITED STATES PATENT AND TRADEMARK OFFICE
CERTIFICATE OF CORRECTION

PATENT NO. : 5,268,246
DATED : DECEMBER 7, 1993
INVENTOR(S) : TAMOTSU ARUGA ET AL

It is certified that error appears in the above-identified patent and that said Letters Patent is hereby corrected as shown below:

Column 10, under Table 1-continued, lines 3-8,

" 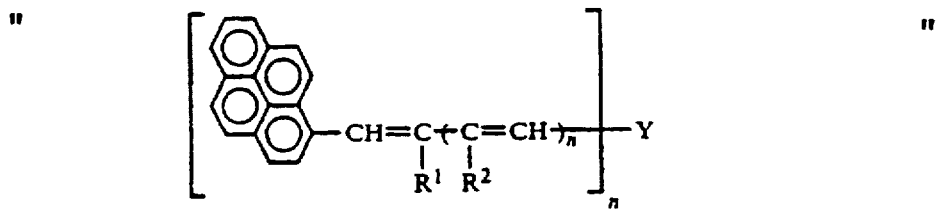 "

should read -- 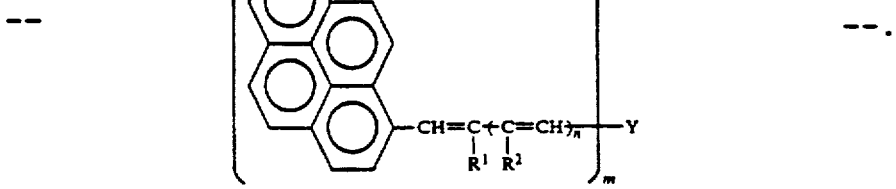 --.

Column 13, line 22, "there is forced" should read --there is formed--.

line 31, "charge carriers The" should read --charge carriers. The".

Column 14, line 36, "range or 30" should read --range of 30--.

Column 17, line 14, "two time" should read --two times--.

UNITED STATES PATENT AND TRADEMARK OFFICE
CERTIFICATE OF CORRECTION

PATENT NO. : 5,268,246

DATED : DECEMBER 7, 1993

INVENTOR(S) : TAMOTSU ARUGA ET AL

It is certified that error appears in the above-identified patent and that said Letters Patent is hereby corrected as shown below:

Column 17, line 57, "a yellow power" should read --a yellow powder--.

Column 18, line 54, "965 cm$^1$" should read --965 cm$^{-1}$--.

Column 28, No. 41,

"  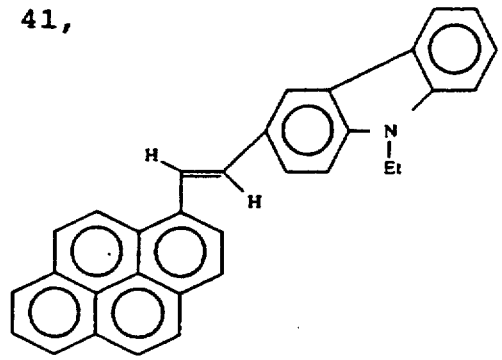  "

should read

--  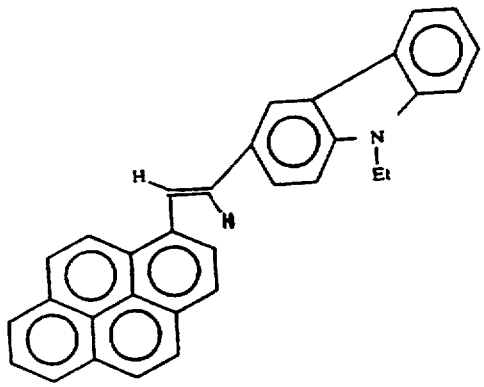  --.

UNITED STATES PATENT AND TRADEMARK OFFICE
CERTIFICATE OF CORRECTION

PATENT NO. : 5,268,246
DATED : DECEMBER 7, 1993
INVENTOR(S) : TAMOTSU ARUGA ET AL

It is certified that error appears in the above-identified patent and that said Letters Patent is hereby corrected as shown below:

Column 33, line 5, "(1-pyrenyl)ethylene)" should read --(1-pyrenyl)-ethylene)--.

Column 51, line 41, "Nemours, E.L. & Co.)" should read --Nemours, E.I. & Co.)--.
    line 68, "was prepared" should read --was prepared.--.

Column 52, line 1, "EXAMPLE 37" should read --EXAMPLE 73--.
    line 17, "a solution The" should read --a solution. The--.
    line 30, "invention was prepared" should read --invention was prepared.--.

UNITED STATES PATENT AND TRADEMARK OFFICE
CERTIFICATE OF CORRECTION

PATENT NO. : 5,268,246

DATED : DECEMBER 7, 1993

INVENTOR(S) : TAMOTSU ARUGA ET AL

It is certified that error appears in the above-identified patent and that said Letters Patent is hereby corrected as shown below:

Column 53, line 27, "visible image The" should read --visible image. The--.

line 43, "and $V_{po}$ and $E_{178}$" should read --and $V_{po}$ and $E_{1/2}$--.

Table 6, under second heading $E_{1/2}$ "0.80" should read --0.89--.

Signed and Sealed this

Twenty-fourth Day of January, 1995

Attest:

Attesting Officer

BRUCE LEHMAN

Commissioner of Patents and Trademarks